US009650417B2

(12) United States Patent
Currie et al.

(10) Patent No.: US 9,650,417 B2
(45) Date of Patent: *May 16, 2017

(54) TREATMENTS FOR GASTROINTESTINAL DISORDERS

(75) Inventors: Mark G. Currie, Sterling, MA (US); Daniel P. Zimmer, Somerville, MA (US); Angelika Fretzen, Somerville, MA (US); Marco Kessler, Danvers, MA (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 361 days.

This patent is subject to a terminal disclaimer.

(21) Appl. No.: 14/116,864

(22) PCT Filed: May 11, 2012

(86) PCT No.: PCT/US2012/037637
§ 371 (c)(1),
(2), (4) Date: Oct. 10, 2014

(87) PCT Pub. No.: WO2012/155101
PCT Pub. Date: Nov. 15, 2012

(65) Prior Publication Data
US 2015/0030697 A1 Jan. 29, 2015

Related U.S. Application Data

(60) Provisional application No. 61/485,046, filed on May 11, 2011.

(51) Int. Cl.
A61K 38/10 (2006.01)
C07K 7/08 (2006.01)
A61K 45/06 (2006.01)

(52) U.S. Cl.
CPC .............. C07K 7/08 (2013.01); A61K 38/10 (2013.01); A61K 45/06 (2013.01)

(58) Field of Classification Search
None
See application file for complete search history.

(56) References Cited

U.S. PATENT DOCUMENTS

| 5,518,888 | A | 5/1996 | Waldman |
| 5,601,990 | A | 2/1997 | Waldman |
| 5,879,656 | A | 3/1999 | Waldman |
| 5,962,220 | A | 10/1999 | Waldman |
| 6,060,037 | A | 5/2000 | Waldman |
| 7,304,036 | B2 | 12/2007 | Currie et al. |
| 7,371,727 | B2 | 5/2008 | Currie et al. |
| 7,704,947 | B2 | 4/2010 | Currie et al. |
| 7,745,409 | B2 | 6/2010 | Currie et al. |
| 7,772,188 | B2 | 8/2010 | Currie et al. |
| 7,910,546 | B2 | 3/2011 | Currie et al. |
| 8,080,526 | B2 | 12/2011 | Currie et al. |
| 8,110,553 | B2 | 2/2012 | Currie et al. |
| 8,507,447 | B2 * | 8/2013 | Currie ...................... C07K 7/08 514/21.5 |
| 8,946,158 | B2 * | 2/2015 | Currie ...................... C07K 7/08 514/13.2 |
| 9,303,066 | B2 | 4/2016 | Currie et al. |
| 2009/0253634 | A1 | 10/2009 | Currie et al. |
| 2010/0048489 | A1 | 2/2010 | Fretzen et al. |
| 2012/0039949 | A1 | 2/2012 | Fretzen et al. |
| 2013/0085107 | A1 | 4/2013 | Currie et al. |
| 2014/0179607 | A9 | 6/2014 | Currie et al. |
| 2014/0342996 | A1 | 11/2014 | Currie et al. |
| 2014/0348942 | A1 | 11/2014 | Currie et al. |
| 2016/0213739 | A1 | 7/2016 | Currie et al. |

FOREIGN PATENT DOCUMENTS

| WO | 0180871 | 11/2001 |
| WO | 2005087797 | 9/2005 |
| WO | 2007022531 | 2/2007 |
| WO | 2008151257 | 12/2008 |
| WO | 2011156453 | 12/2011 |

OTHER PUBLICATIONS

Moleski, Merck Manual, 2016, 1-8, http://www.merckmanuals.com/professional/gastrointestinal-disorders/irritable-bowel-syndrome.*

* cited by examiner

Primary Examiner — James H Alstrum Acevedo
Assistant Examiner — Roy Teller
(74) Attorney, Agent, or Firm — Honigman Miller Schwartz and Cohn LLP; Kelly T. Murphy; Jonathan P. O'Brien

(57) ABSTRACT

The present invention provides pharmaceutical compositions and methods of treating lower gastrointestinal disorders, including irritable bowel syndrome and constipation.

31 Claims, 13 Drawing Sheets

FIGURE 1
A
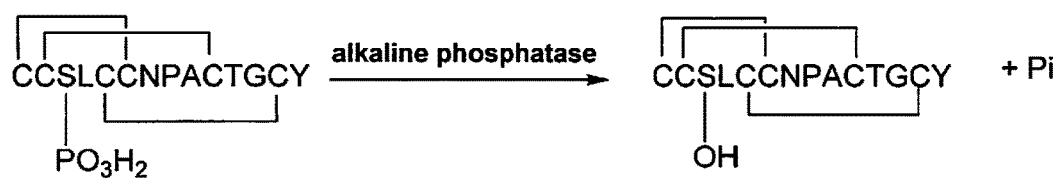
B
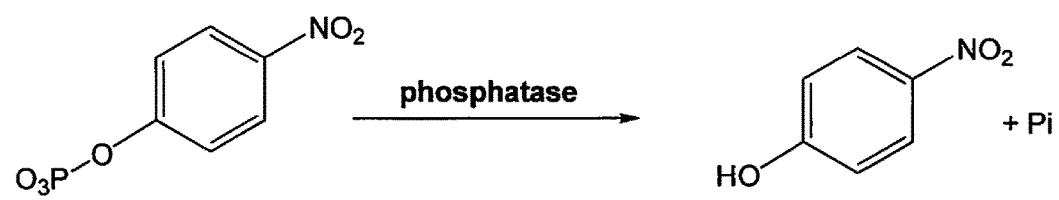

Peptide 4 and peptide 2 promote duodenal fluid secretion in rat duodenal loops
(y axis in units of µl/min/cm)

Stability of Peptide 2, Dephospho-peptide 2, and Peptide 3 in rat intestinal (jejunum) fluid Legend: ● – peptide 2; ■ – peptide 2 control; ▲ – dephospho-peptide 2; ▼ – dephospho-peptide 2 control; ♦ – peptide 3; ○ – peptide 3 control.

Experimental Schedule of Peptide 2 Administration in TNBS-induced Colorectal Hypersensitivity to Distension in Rats

T1: Peptide 2 (3, 10, 30 μg/kg, po) or vehicle (20 mM Tris HCl, pH 6.85, po);
T2: TNBS (80 mg/kg, ir);
T3: Peptide 2 (3, 10, 30 μg/kg, po) or vehicle (20 mM Tris HCl, pH 6.85, po)

Effect of Peptide 2 on the Abdominal Response to Colorectal Distension in Rats under Basal Conditions Legend: □ : basal values; ▲: TNBS + vehicle; ▼: TNBS + peptide 2. *, p<0.05 compared to basal values. Data are expressed as the mean ±SEM.

FIGURE 6A

Effect of peptide 2 on the Abdominal Response to Colorectal Distension in Rats after TNBS-induced Colorectal Hypersensitivity

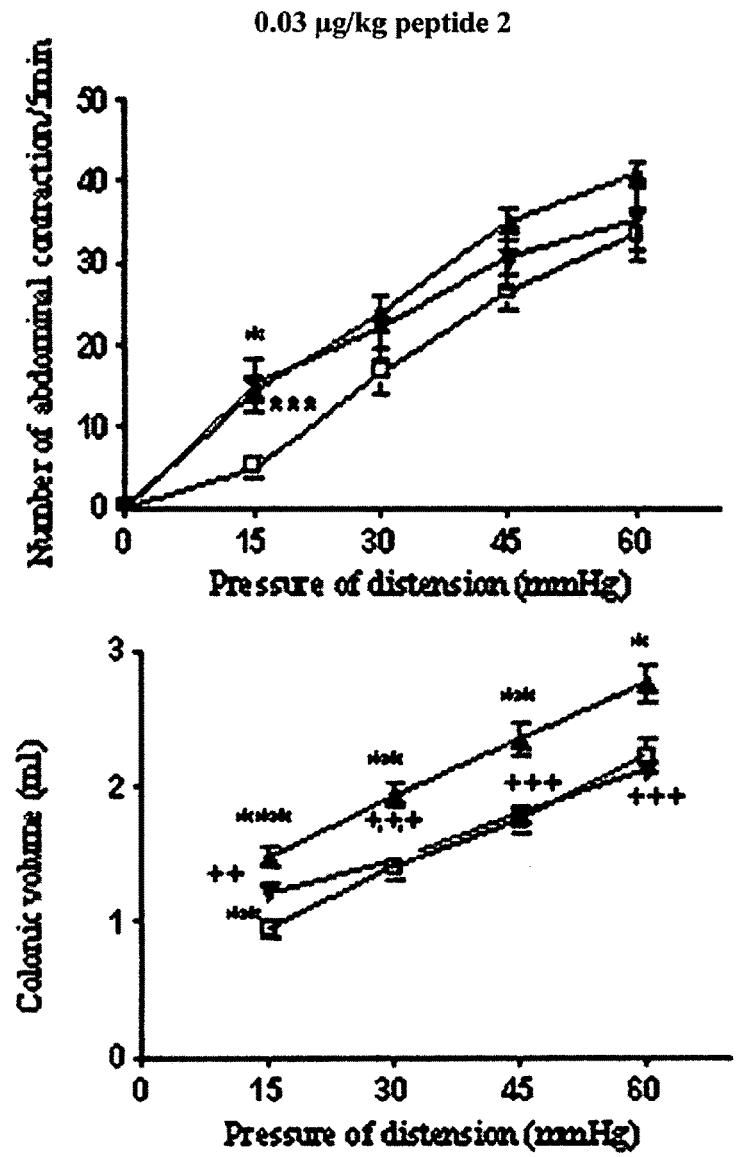

Legend: □: basal values; ▲: TNBS + vehicle; ▼: TNBS + Peptide 2. *, p<0.05 compared to basal values; , p<0.01 compared to basal values; *, p<0.001 compared to basal values; +, p<0.05 compared to TNBS + vehicle; ++, p<0.01 compared to TNBS + vehicle; +++, p<0.001 compared to TNBS + vehicle. Data are expressed as the mean ± SEM.

FIGURE 6B

Effect of peptide 2 on the Abdominal Response to Colorectal Distension in Rats after TNBS-induced Colorectal Hypersensitivity 0.3 µg/kg peptide 2

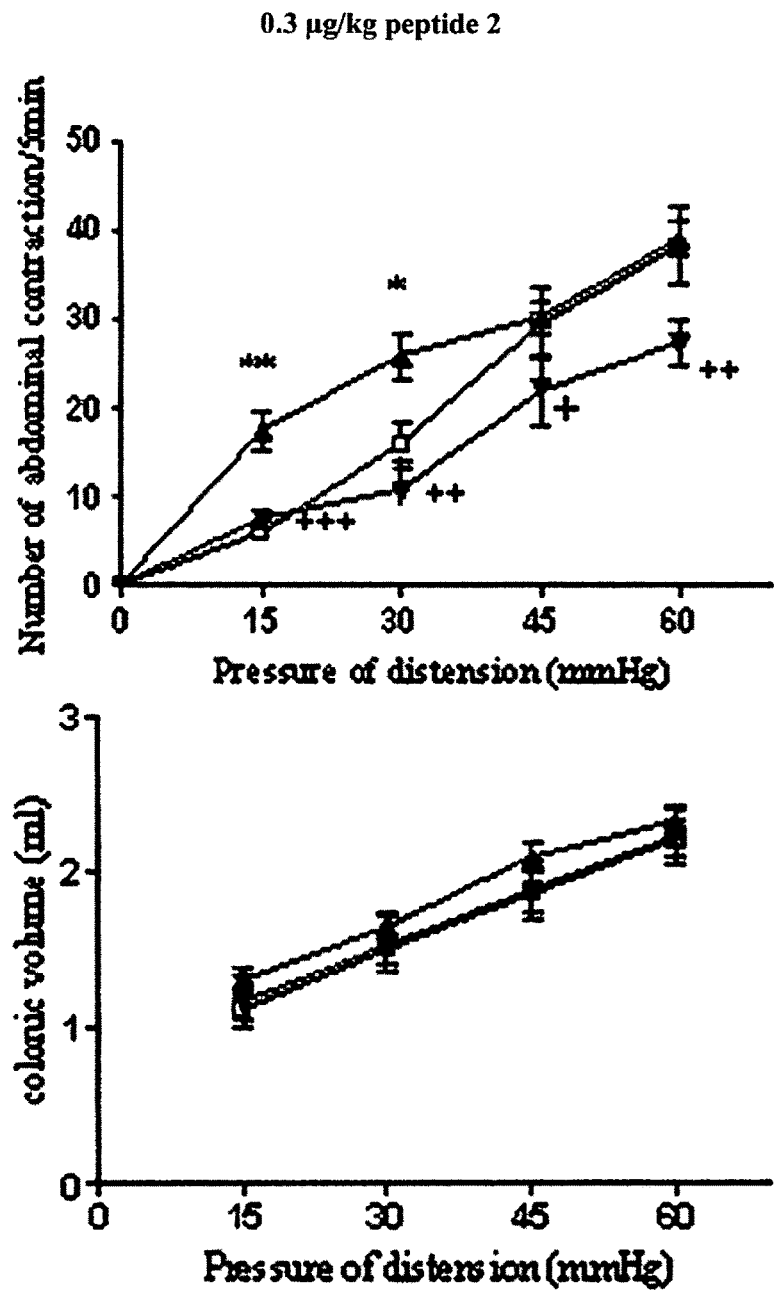

Legend: □: basal values; ▲: TNBS + vehicle; ▼: TNBS + Peptide 2. *, p<0.05 compared to basal values; , p<0.01 compared to basal values; *, p<0.001 compared to basal values; +, p<0.05 compared to TNBS + vehicle; ++, p<0.01 compared to TNBS + vehicle; +++, p<0.001 compared to TNBS + vehicle. Data are expressed as the mean ± SEM.

FIGURE 6C

Effect of peptide 2 on the Abdominal Response to Colorectal Distension in Rats after TNBS-induced Colorectal Hypersensitivity 10 µg/kg peptide 2

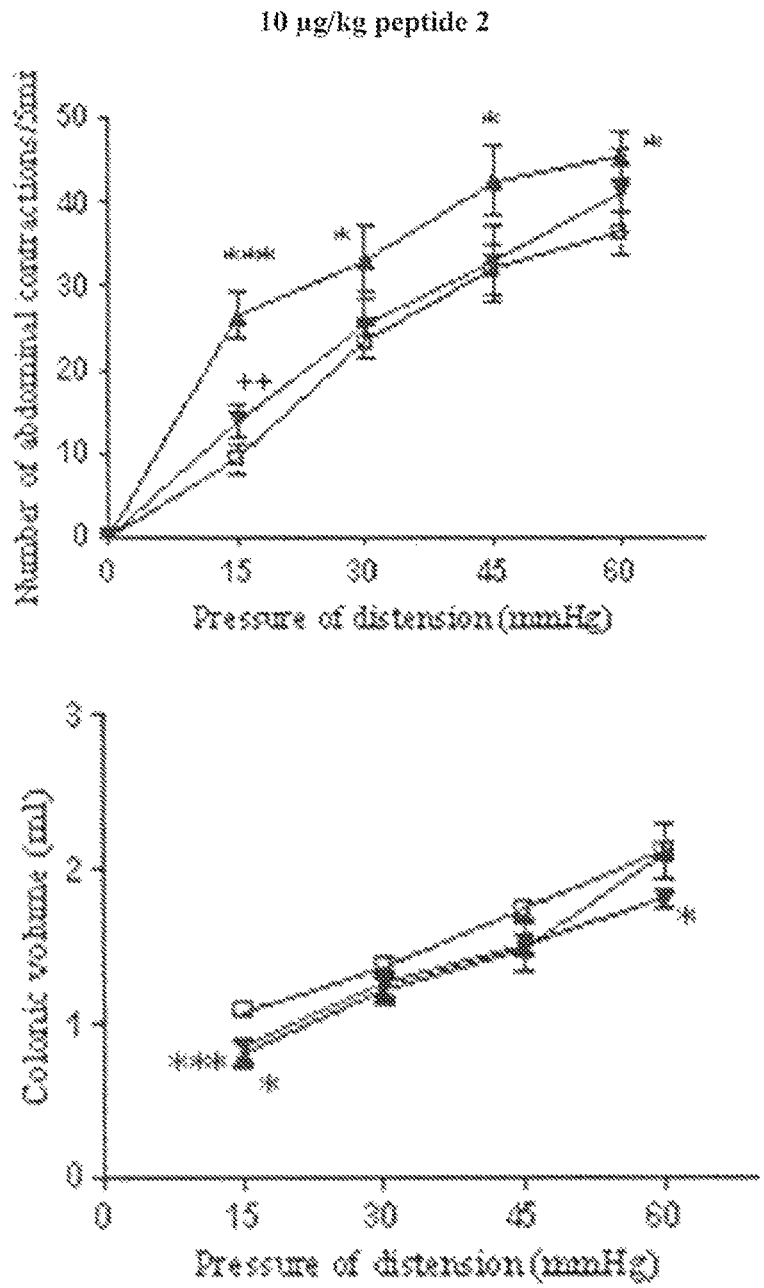

Legend: □: basal values; ▲: TNBS + vehicle; ▼: TNBS + Peptide 2. *, p<0.05 compared to basal values; , p<0.01 compared to basal values; *, p<0.001 compared to basal values; +, p<0.05 compared to TNBS + vehicle; ++, p<0.01 compared to TNBS + vehicle; +++, p<0.001 compared to TNBS + vehicle. Data are expressed as the mean ± SEM.

Effect of (3, 10, 30 µg/kg) of Peptide 2 on the Abdominal Response to Colorectal Distension in Rats under Basal Conditions

Legend: □ : basal values; ▲: TNBS + vehicle; ▼: TNBS + Peptide 2. *, p<0.05 compared to basal values; +, p<0.05 compared to TNBS + vehicle p<0.01 compared to TNBS + vehicle expressed as the mean ±SEM.

FIGURE 8

Effect of (3, 10, 30 µg/kg) of Peptide 2 on the Abdominal Response to Colorectal Distension in Rats after TNBS-induced Colorectal Hypersensitivity

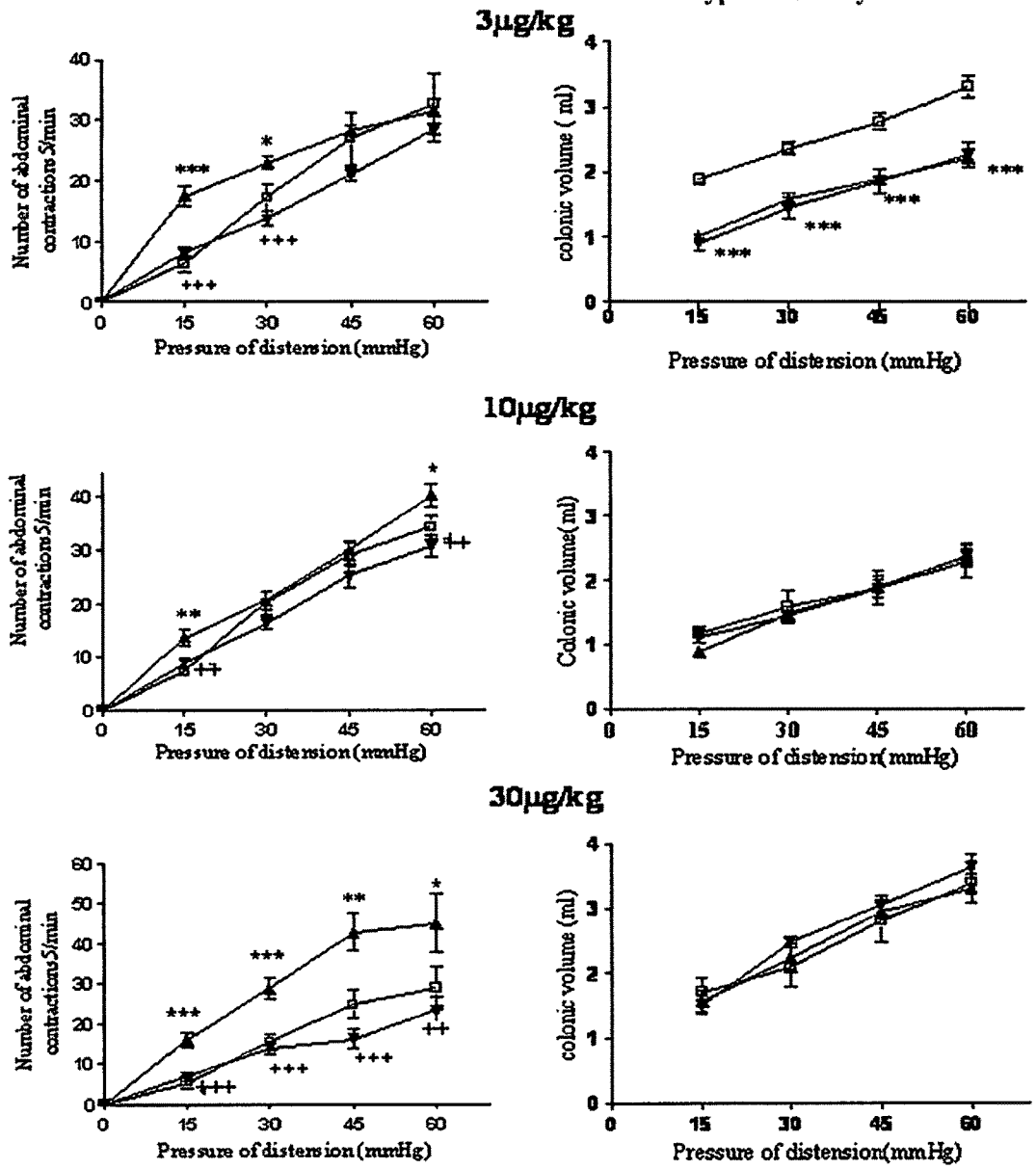

Legend: □: basal values; ▲: TNBS + vehicle; ▼: TNBS + Peptide 2. *, p<0.05 compared to basal values; , p<0.01 compared to basal values; *, p<0.001 compared to basal values; ++, p<0.01 compared to TNBS + vehicle; +++, p<0.001 compared to TNBS + vehicle. Data are expressed as the mean ± SEM

Experimental Design to Measure the Effects of Peptide 2 on Basal and Stress-Induced Colonic Hypersensitivity to Barostatic Colorectal Distension in Rats

Effect of Peptide 2 on the Abdominal Response to Colorectal Distension in Female Wistar Rats after Stress-induced Colorectal Hypersensitivity
(■, dashed line – ctrl + veh. (20 mM Tris HCL, po) ; ■, solid line – stress + veh. (20 mM Tris HCL, po); ▲ – stress + pep. 2 (po) at indicated dosages)

SEQUENCE LISTING

<160> NUMBER OF SEQ ID NOS: 10

<210> SEQ ID NO 1
<211> LENGTH: 17
<212> TYPE: PRT
<213> ORGANISM: Artificial Sequence
<220> FEATURE:
<223> OTHER INFORMATION: Synthetically generated peptide
<220> FEATURE:

```
<221> NAME/KEY: MISC_FEATURE
<222> LOCATION: (1)..(1)
<223> OTHER INFORMATION: Xaa1 is Asn, D-Asn, Gln, D-Gln, Pro, Ala,
      beta-Ala, D-Ala, Val, D-Val, Gly, Thr, D-Thr, Asp, D-Asp,
      gamma-carboxylated Asp, Glu, D-Glu, gamma-carboxylated Glu,
      a-aminosuberic acid (Asu), a-aminoadipic acid (Aad),
      a-aminopimelic acid (Apm), or is absent
<220> FEATURE:
<221> NAME/KEY: VARIANT
<222> LOCATION: (1)..(2)
<223> OTHER INFORMATION: if Xaa1 is absent and Xaa2 is present, then
      Xaa2 may be modified on its amino group by methyl, ethanedioic
      acid, propanedioic acid, butanedioic acid, pentanedioic acid,
      hexanedioic acid, heptanedioic acid or octanedioic acid
<220> FEATURE:
<221> NAME/KEY: VARIANT
<222> LOCATION: (1)..(1)
<223> OTHER INFORMATION: Xaa1 is present, Xaa1 may be modified on its
      amino acid group by methyl, ethanedioic acid, propanedioic acid,
      butanedioic acid, pentanedioic acid, hexanedioic acid,
      heptanedioic acid or octanedioic acid
<220> FEATURE:
<221> NAME/KEY: VARIANT
<222> LOCATION: (1)..(3)
<223> OTHER INFORMATION: if both Xaa1 and Xaa2 are absent, then Xaa3
      may be modified on its amino group by methyl, ethanedioic acid,
      propanedioic acid, butanedioic acid, pentaneioic acid, hexanedioic
      acid, heptanedioic acid or octanedioic acid
<220> FEATURE:
<221> NAME/KEY: MISC_FEATURE
<222> LOCATION: (2)..(2)
<223> OTHER INFORMATION: Xaa2 is Asp, gamma-carboxylated Asp, Glu,
      gamma-carboxylated Glu, Asu, Aad, Apm, or is absent
<220> FEATURE:
<221> NAME/KEY: MISC_FEATURE
<222> LOCATION: (3)..(3)
<223> OTHER INFORMATION: Xaa3 is Asp, gamma-carboxylated Asp, Glu,
      gamma-carboxylated Glu, Asu, Aad, Apm or is absent
<220> FEATURE:
<221> NAME/KEY: MISC_FEATURE
<222> LOCATION: (4)..(4)
<223> OTHER INFORMATION: Xaa4 is Cys or D-Cys
<220> FEATURE:
<221> NAME/KEY: MISC_FEATURE
<222> LOCATION: (6)..(6)
<223> OTHER INFORMATION: Xaa6 is P-Ser, P-Thr, P-homo-Ser,
      4-hydroxyvaline phosphate, P-homo-Thr, P-Cys or P-Tyr
<220> FEATURE:
<221> NAME/KEY: MISC_FEATURE
<222> LOCATION: (7)..(7)
<223> OTHER INFORMATION: Xaa7 is Tyr, Leu, Phe or Ile
<220> FEATURE:
<221> NAME/KEY: MISC_FEATURE
<222> LOCATION: (8)..(8)
<223> OTHER INFORMATION: Xaa is Cys or D-Cys
<220> FEATURE:
<221> NAME/KEY: MISC_FEATURE
<222> LOCATION: (14)..(14)
<223> OTHER INFORMATION: Xaa14 is Thr, Ala or Phe
<220> FEATURE:
<221> NAME/KEY: MISC_FEATURE
<222> LOCATION: (16)..(16)
<223> OTHER INFORMATION: Xaa16 is Cys or D-Cys
<220> FEATURE:
<221> NAME/KEY: MISC_FEATURE
<222> LOCATION: (17)..(17)
<223> OTHER INFORMATION: Xaa17 is Tyr, D-Tyr, or is absent

<400> SEQUENCE: 1

Xaa Xaa Xaa Xaa Cys Xaa Xaa Xaa Cys Asn Pro Ala Cys Xaa Gly Xaa
1               5                   10                  15

Xaa

<210> SEQ ID NO 2
<211> LENGTH: 16
<212> TYPE: PRT
```

```
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa6 is P-Ser

<400> SEQUENCE: 2

Asp Asp Cys Cys Xaa Leu Cys Cys Asn Pro Ala Cys Thr Gly Cys Tyr
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa5 is P-Ser

<400> SEQUENCE: 3

Asp Asp Cys Cys Xaa Leu Cys Cys Asn Pro Ala Cys Thr Gly Cys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa5 is P-Ser

<400> SEQUENCE: 4

Asp Asp Cys Cys Xaa Tyr Cys Cys Asn Pro Ala Cys Thr Gly Cys Tyr
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa5 is P-Ser

<400> SEQUENCE: 5

Asp Asp Cys Cys Xaa Tyr Cys Cys Asn Pro Ala Cys Thr Gly Cys
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (3)..(3)
<223> OTHER INFORMATION: Xaa3 is P-Ser

<400> SEQUENCE: 6

Cys Cys Xaa Leu Cys Cys Asn Pro Ala Cys Thr Gly Cys Tyr
```

```
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (3)..(3)
<223> OTHER INFORMATION: Xaa3 is P-Ser

<400> SEQUENCE: 7

Cys Cys Xaa Leu Cys Cys Asn Pro Ala Cys Thr Gly Cys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (3)..(3)
<223> OTHER INFORMATION: Xaa3 is P-Ser

<400> SEQUENCE: 8

Cys Cys Xaa Tyr Cys Cys Asn Pro Ala Cys Thr Gly Cys Tyr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (3)..(3)
<223> OTHER INFORMATION: Xaa3 is P-Ser

<400> SEQUENCE: 9

Cys Cys Xaa Tyr Cys Cys Asn Pro Ala Cys Thr Gly Cys
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (3)..(3)
<223> OTHER INFORMATION: Xaa3 is P-Ser
<220> FEATURE:
<221> NAME/KEY: VARIANT
<222> LOCATION: (4)..(4)
<223> OTHER INFORMATION: Xaa4 is Tyr or Leu
<220> FEATURE:
<221> NAME/KEY: VARIANT
<222> LOCATION: (14)..(14)
<223> OTHER INFORMATION: Xaa14 is Tyr

<400> SEQUENCE: 10

Cys Cys Xaa Xaa Cys Cys Asn Pro Ala Cys Thr Gly Cys Xaa
1               5                   10
```

TREATMENTS FOR GASTROINTESTINAL DISORDERS

PRIORITY CLAIM

This application is a national phase application of PCT/US2012/037637, filed May 11, 2012, which claims priority to U.S. Provisional Patent Application Ser. No. 61/485,046 filed May 11, 2011. The entire contents of the aforementioned applications are incorporated herein by reference.

FIELD OF THE INVENTION

This invention relates to peptides, compositions and methods for treating gastrointestinal disorders, including irritable bowel syndrome and constipation.

SEQUENCE LISTING

This application incorporates by reference in its entirety the Sequence Listing entitled "IW083PCT1sequence_ST25.txt" (5.66 kilobytes), which was created May 8, 2012 and filed electronically herewith.

BACKGROUND

Constipation-predominant irritable bowel syndrome (IBS-C) and chronic constipation (CC) are common lower gastrointestinal (GI) disorders. IBS-C is characterized by symptoms that include recurrent abdominal pain or discomfort, fewer than three bowel movements per week, lumpy or hard stools, defecation straining, a feeling of incomplete bowel movement, passing mucus and/or bloating (Drossman et al., Rome III: The Functional Gastrointestinal Disorders, $3^{rd}$ Ed., McLean, Va.: Degnon Assoc., Inc., 2006). Chronic constipation (also called functional constipation) is characterized by defecation straining, lumpy or hard stools, sensation of incomplete evacuation, sensation of anorectal obstruction/blockage, and/or fewer than three bowel movements per week (Drossman 2006).

Conventional treatment options for constipation-predominant irritable bowel syndrome (IBS-C) and chronic constipation (CC), as well as other lower GI disorders, have been of limited efficacy for many patients. Thus, there remains a need for new compounds and methods for treating IBS-C and CC, as well as other GI disorders.

SUMMARY

The present invention features compositions and methods for treating IBS-C and CC as well as other lower GI disorders. The compositions and methods feature peptides that activate guanylate cyclase C (GC-C) more strongly in the upper small intestine and activate GC-C more weakly in the lower small intestine and thus may allow for more normal function in the lower small intestine while addressing symptoms of CC and IBS-C, including such symptoms as pain, bloating, discomfort, stool consistency, straining and constipation severity.

One aspect of the present invention provides a method of treating IBS-C or CC, which comprises administering a peptide comprising the amino acid sequence:

$Xaa_1$ $Xaa_2$ $Xaa_3$ $Xaa_4$ $Cys_5$ $Xaa_6$ $Xaa_7$ $Xaa_8$ $Cys_9$ $Asn_{10}$ $Pro_{11}$ $Ala_{12}$ $Cys_{13}$ $Xaa_{14}$ $Gly_{15}$ $Xaa_{16}$ $Xaa_{17}$ [SEQ ID No: 1], or a pharmaceutically acceptable salt thereof; wherein $Xaa_1$ is Asn, D-Asn, Gln, D-Gln, Pro, Ala, β-Ala, D-Ala, Val, D-Val, Gly, Thr, D-Thr, Asp, D-Asp, γ-carboxylated Asp, Glu, D-Glu, γ-carboxylated Glu, α-aminosuberic acid (Asu), α-aminoadipic acid (Aad), α-aminopimelic acid (Apm), or is absent;

$Xaa_2$ is Asp, γ-carboxylated Asp, Glu, γ-carboxylated Glu, Asu, Aad, Apm, or is absent;

$Xaa_3$ is Asp, γ-carboxylated Asp, Glu, γ-carboxylated Glu, Asu, Aad, Apm, or is absent;

$Xaa_4$ is Cys or D-Cys;

$Xaa_6$ is P-Ser, P-Thr, P-homo-Ser, 4-hydroxyvaline phosphate, P-homo-Thr, P-Cys or P-Tyr;

$Xaa_7$ is Tyr, Leu, Phe or Ile;

$Xaa_8$ is Cys or D-Cys;

$Xaa_{14}$ is Thr, Ala or Phe;

$Xaa_{16}$ is Cys or D-Cys; and $Xaa_{17}$ is Tyr, D-Tyr, or is absent;

wherein:

if $Xaa_1$ is present, $Xaa_1$ may be modified on its amino group by methyl, ethanedioic acid, propanedioic acid, butanedioic acid, pentanedioic acid, hexanedioic acid, heptanedioic acid or octanedioic acid;

if $Xaa_1$ is absent and $Xaa_2$ is present, then $Xaa_2$ may be modified on its amino group by methyl, ethanedioic acid, propanedioic acid, butanedioic acid, pentanedioic acid, hexanedioic acid, heptanedioic acid or octanedioic acid; or if both $Xaa_1$ and $Xaa_2$ are absent, then $Xaa_3$ may be modified on its amino group by methyl, ethanedioic acid, propanedioic acid, butanedioic acid, pentanedioic acid, hexanedioic acid, heptanedioic acid or octanedioic acid.

A second aspect of the present invention provides pharmaceutical compositions comprising a peptide described herein that is useful for treating IBS-C or CC as well as other lower GI disorders.

The details of one or more embodiments of the invention are set forth in the accompanying description.

BRIEF DESCRIPTION OF THE FIGURES

FIG. 1A illustrates the reaction of an exemplary peptide of the present invention with alkaline phosphatase.

FIG. 1B illustrates the hydrolysis of the control p-nitrophenylphosphate by phosphatases.

FIG. 6A presents the effect of 0.03 μg/kg Peptide 2 on the abdominal response to colorectal distension in rats after TNBS-induced colorectal hypersensitivity.

FIG. 6B presents the effect of 0.3 μg/kg Peptide 2 on the abdominal response to colorectal distension in rats after TNBS-induced colorectal hypersensitivity.

FIG. 6C presents the effect of 10 μg/kg Peptide 2 on the abdominal response to colorectal distension in rats after TNBS-induced colorectal hypersensitivity.

FIG. 8 presents the effect of (3, 10, 30 μg/kg) of Peptide 2 on the abdominal response to colorectal distension in rats after TNBS-induced colorectal hypersensitivity.

Figure 2:
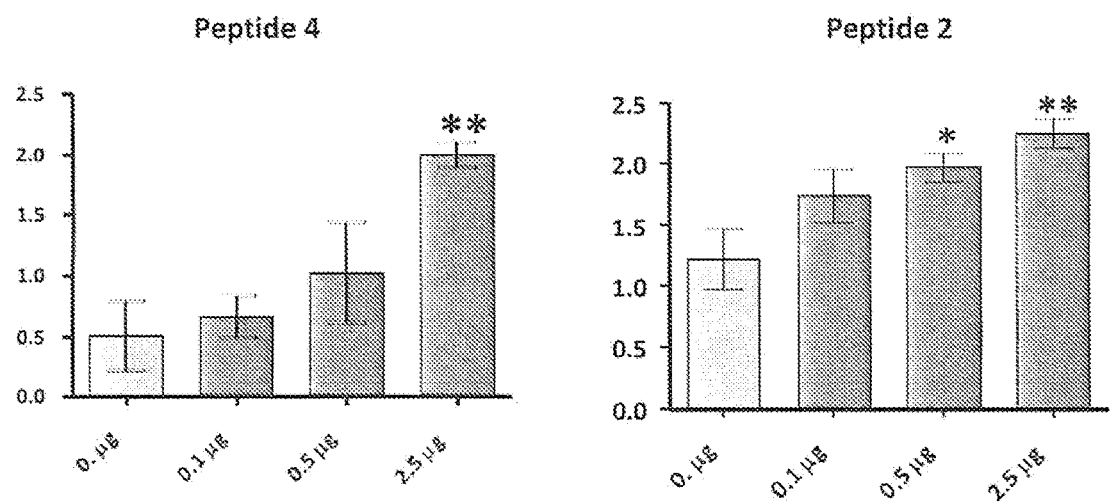
FIG. 2 presents an example showing that Peptide 2 and Peptide 4 promote duodenal fluid secretion.

These figures are provided by way of example and are not intended to limit the scope of the present invention.

DETAILED DESCRIPTION

Guanylate cyclase C (GC-C) is a transmembrane receptor that is located on the apical surface of epithelial cells in the stomach and intestine. The receptor has an extracellular ligand-binding domain, a single transmembrane region and a C-terminal guanylyl cyclase domain. When a ligand binds to the extracellular domain of GC-C, the intracellular catalytic domain catalyzes the production of cGMP from GTP. In vivo, this increase in intracellular cGMP initiates a cascade of events that leads to increased secretion of chloride and bicarbonate into the intestinal lumen, increased luminal pH, decreased luminal sodium absorption, increased fluid secretion, and acceleration of intestinal transit. cGMP, which is secreted bidirectionally from the epithelium into the mucosa and lumen, has also been shown to dampen afferent C fiber firing, suggesting a potential mechanism for the observed analgesic effects of GC-C agonists on visceral pain.

Linaclotide, a peptide GC-C agonist that is orally administered and currently in clinical trials for treatment of irritable bowel syndrome with constipation (IBS-C) and chronic constipation (CC), has numerous effects on lower GI physiology including: (1) reduced visceral pain, (2) reduced bloating, and (3) increased GI transit, which can lead to increased stool frequency and improved stool consistency. Orally administered linaclotide acts locally by activating GC-C at the luminal surface; there are no detectable levels of linaclotide seen systemically after oral administration at therapeutic dose levels. Thus, the results from clinical trials of linaclotide, as well as preclinical studies that have been done with linaclotide and related peptides, suggest that GC-C peptide agonists may be used therapeutically.

It would be useful to have additional GC-C agonists that could be used to alleviate lower GI disorders and symptoms (e.g., IBS-C and CC) with the potential of decreasing the possibility of causing diarrhea. The GC-C agonist peptides described herein are more active in the upper small intestine (i.e., the duodenum), and less active in the lower small intestine (i.e., the jejunum and ileum). Without wishing to be bound by any theory, compounds that are more active in the upper small intestine and less active in the lower small intestine may promote enhanced protection of the duodenum and rest of GI tract via increased bicarbonate secretion by the duodenum; promote fluid secretion into the upper GI tract, leading to a decrease in constipation severity and straining and an improvement in stool consistency in CC and IBS-C; and allow most of the jejunum and ileum to function more normally as an absorptive tissue rather than a secretory tissue, minimizing the potential for diarrhea as a side effect. Such agonists may further benefit patients who suffer from lower GI disorders (e.g., IBS-C and CC) by reducing or ameliorating abdominal pain and discomfort and reducing bloating.

In one aspect, the invention provides a novel GC-C peptide agonist useful for the treatment of gastrointestinal disorders, particularly lower GI disorders such as IBS-C and CC. The GC-C peptide agonist is designed to be more active in the upper small intestine and less active as it traverses the lower small intestine and large intestine. The peptides of the invention are also useful for ameliorating abdominal pain and discomfort. In one embodiment, the peptides are useful for ameliorating abdominal pain and/or discomfort associated with CC or IBS-C. The GC-C agonist peptide contains a phosphoamino acid, e.g., a phosphoserine, to replace a conserved glutamate or aspartate found in other GC-C agonist peptides. The phosphate of a phosphoamino acid —$OPO_3^{2-}$, such as phosphoserine, is able to act as a biomimetic for the $COO^-$ of glutamate or aspartate such that the phosphoamino acid-containing peptide is able to bind to and activate GC-C. The phosphoamino acid-containing peptide can be dephosphorylated by intestinal alkaline phosphatases, which greatly decreases the GC-C binding and agonist activity of the peptide. Intestinal alkaline phosphatases are found throughout the GI tract, and are most active in an alkaline luminal environment, including the small intestine. The phosphoamino acid-containing peptide is able to activate GC-C in the upper GI tract to promote fluid and bicarbonate secretion. As the peptide promotes increased fluid and bicarbonate secretion in the upper GI, the intestinal lumen becomes more alkaline, thus activating the alkaline phosphatase activity. Thus, through the action of the peptide on GC-C as well as the movement of the peptide through the intestine, the peptide's phosphoamino acid is converted to the dephosphorylated amino acid, thereby decreasing its activity as a GC-C agonist as it transits from the upper to lower GI.

As used herein, the term "P-" preceding an amino acid or the three letter abbreviation thereof, refers to a phosphoamino acid. For example, the terms "P-Ser", "P-Thr", "P-Tyr", "P-Cys", "P-homo-Cys", "P-homo-Ser" and "P-homo-Thr" refer to phosphoserine, phosphothreonine, phosphotyrosine, phosphocysteine, phosphohomocysteine, phosphohomoserine, and phosphohomothreonine, respectively. As used herein, a phosphoamino acid refers to an ester or thioester of an amino acid and phosphoric acid; e.g., the hydrogen on the alcohol or thiol functional group is replaced by —$P(O)(OH)_2$. For example, P-Ser has the structure

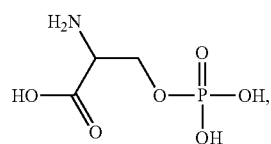

P-Thr has the structure

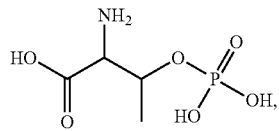

P-Tyr has the structure

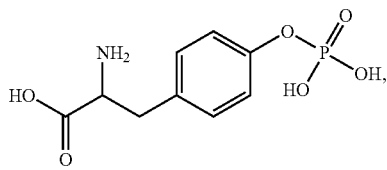 [SMILES: NC(Cc1ccc(OP(=O)(O)O)cc1)C(=O)O]

and P-Cys has the structure

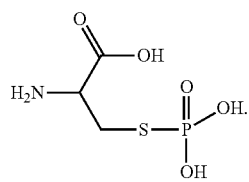 [SMILES: NC(CSP(=O)(O)O)C(=O)O]

In several embodiments, a peptide or pharmaceutically acceptable salt thereof is provided that is useful for the treatment of lower GI disorders, and in particular disorders such as IBS-C and CC, wherein the peptide comprises the amino acid sequence:

$Xaa_1$ $Xaa_2$ $Xaa_3$ $Xaa_4$ $Cys_5$ $Xaa_6$ $Xaa_7$ $Xaa_8$ $Cys_9$ $Asn_{10}$ $Pro_{11}$ $Ala_{12}$ $Cys_{13}$ $Xaa_{14}$ $Gly_{15}$ $Xaa_{16}$ $Xaa_{17}$ [SEQ ID No: 1], or a pharmaceutically acceptable salt thereof; wherein $Xaa_1$ is Asn, D-Asn, Gln, D-Gln, Pro, Ala, β-Ala, D-Ala, Val, D-Val, Gly, Thr, D-Thr, Asp, D-Asp, γ-carboxylated Asp, Glu, D-Glu, γ-carboxylated Glu, α-aminosuberic acid (Asu), α-aminoadipic acid (Aad), α-aminopimelic acid (Apm), or is absent;

$Xaa_2$ is Asp, γ-carboxylated Asp, Glu, γ-carboxylated Glu, Asu, Aad, Apm, or is absent;

$Xaa_3$ is Asp, γ-carboxylated Asp, Glu, γ-carboxylated Glu, Asu, Aad, Apm, or is absent;

$Xaa_4$ is Cys or D-Cys;

$Xaa_6$ is P-Ser, P-Thr, P-homo-Ser, 4-hydroxyvaline phosphate, P-homo-Thr, P-Cys or P-Tyr;

$Xaa_7$ is Tyr, Leu, Phe or Ile;

$Xaa_8$ is Cys or D-Cys;

$Xaa_{14}$ is Thr, Ala or Phe;

$Xaa_{16}$ is Cys or D-Cys; and $Xaa_{17}$ is Tyr, D-Tyr, or is absent;

wherein:

if $Xaa_1$ is present, $Xaa_1$ may be modified on its amino group by methyl, ethanedioic acid, propanedioic acid, butanedioic acid, pentanedioic acid, hexanedioic acid, heptanedioic acid or octanedioic acid;

if $Xaa_1$ is absent and $Xaa_2$ is present, then $Xaa_2$ may be modified on its amino group by methyl, ethanedioic acid, propanedioic acid, butanedioic acid, pentanedioic acid, hexanedioic acid, heptanedioic acid or octanedioic acid; or if both $Xaa_1$ and $Xaa_2$ are absent, then $Xaa_3$ may be modified on its amino group by methyl, ethanedioic acid, propanedioic acid, butanedioic acid, pentanedioic acid, hexanedioic acid, heptanedioic acid or octanedioic acid.

In some embodiments, both $Xaa_2$ and $Xaa_3$ are absent. In other embodiments, $Xaa_2$ is Asp or Glu and $Xaa_3$ is absent. In yet other embodiments, $Xaa_2$ is Asp or Glu and $Xaa_3$ is Asp or Glu.

In some embodiments, $Xaa_7$ is Tyr or Leu.

In some embodiments, $Xaa_{14}$ is Thr.

In some embodiments, $Xaa_{17}$ is Tyr or is absent.

In some embodiments, $Xaa_1$ is Asn, D-Asn, Gln, D-Gln, Pro, Ala, β-Ala, D-Ala, Val, D-Val, Gly, Thr, D-Thr, Asp, D-Asp, Glu or D-Glu. In further embodiments, $Xaa_1$ is Asp, D-Asp, Glu or D-Glu.

In some embodiments, $Xaa_6$ is P-Ser or P-Thr. In further embodiments, $Xaa_6$ is P-Ser.

In some embodiments, $Xaa_1$, $Xaa_2$ and $Xaa_3$ are absent and $Xaa_4$ is D-Cys or Cys. In further embodiments, $Xaa_7$ is Tyr or Leu. In further embodiments, $Xaa_{14}$ is Thr. In further embodiments, $Xaa_{17}$ is Tyr or is absent. In further embodiments, $Xaa_6$ is P-Ser.

In some embodiments, at least one of $Xaa_4$, $Xaa_8$ or $Xaa_{16}$ is Cys. In some embodiments, at least two of $Xaa_4$, $Xaa_8$ or $Xaa_{16}$ are Cys. In some embodiments, all of $Xaa_4$, $Xaa_8$ and $Xaa_{16}$ are Cys. In some embodiments, at least one of $Xaa_4$, $Xaa_8$ or $Xaa_{16}$ is D-Cys. In some embodiments, at least two of $Xaa_4$, $Xaa_8$ or $Xaa_{16}$ are D-Cys. In some embodiments, all of $Xaa_4$, $Xaa_8$ and $Xaa_{16}$ are D-Cys.

In some embodiments, a peptide or pharmaceutically acceptable salt thereof is provided that is useful for the treatment of lower GI disorders, in particular disorders such as IBS-C and CC, wherein the peptide comprises the amino acid sequence $Cys_4$ $Cys_5$ $P$-$Ser_6$ $Xaa_7$ $Cys_8$ $Cys_9$ $Asn_{10}$ $Pro_{11}$ $Ala_{12}$ $Cys_{13}$ $Thr_{14}$ $Gly_{15}$ $Cys_{16}$ $Xaa_{17}$, wherein $Xaa_7$ is Tyr or Leu and $Xaa_{17}$ is Tyr or is absent [SEQ ID No: 10].

In some embodiments, a peptide or pharmaceutically acceptable salt thereof is provided that is useful for the treatment of lower GI disorders, in particular disorders such as IBS-C and CC, wherein the peptide comprises the amino acid sequence

```
                                        [SEQ ID No: 2]
Asp Asp Cys Cys P-Ser Leu Cys Cys Asn Pro Ala Cys
Thr Gly Cys Tyr,

[SEQ ID No: 3]
Asp Asp Cys Cys P-Ser Leu Cys Cys Asn Pro Ala Cys
Thr Gly Cys;

[SEQ ID No: 4]
Asp Asp Cys Cys P-Ser Tyr Cys Cys Asn Pro Ala Cys
Thr Gly Cys Tyr;

[SEQ ID No: 5]
Asp Asp Cys Cys P-Ser Tyr Cys Cys Asn Pro Ala Cys
Thr Gly Cys;

[SEQ ID No: 6]
Cys Cys P-Ser Leu Cys Cys Asn Pro Ala Cys Thr Gly
Cys Tyr;

[SEQ ID No: 7]
Cys Cys P-Ser Leu Cys Cys Asn Pro Ala Cys Thr Gly
Cys;

[SEQ ID No: 8]
Cys Cys P-Ser Tyr Cys Cys Asn Pro Ala Cys Thr Gly
Cys Tyr;
or
                                        [SEQ ID No: 9]
Cys Cys P-Ser Tyr Cys Cys Asn Pro Ala Cys Thr Gly
Cys.
```

In some embodiments, a peptide or pharmaceutically acceptable salt thereof is provided that is useful for the treatment of lower GI disorders, in particular disorders such as IBS-C and CC, wherein the peptide comprises peptide comprises no more than 50, 40, 30 or 20 amino acids. In further embodiments, the peptide comprises no more than 19, 18, 17, 16, 15 or 14 amino acids.

In another aspect, a peptide or pharmaceutically acceptable salt thereof is provided that is useful for the treatment of lower GI disorders, in particular disorders such as IBS-C and CC, wherein the peptide consists of the amino acid sequence $Xaa_1$ $Xaa_2$ $Xaa_3$ $Xaa_4$ $Cys_5$ $Xaa_6$ $Xaa_7$ $Xaa_8$ $Cys_9$ $Asn_{10}$ $Pro_{11}$ $Ala_{12}$ $Cys_{13}$ $Xaa_{14}$ $Gly_{15}$ $Xaa_{16}$ $Xaa_{17}$ [SEQ ID No: 1], or a pharmaceutically acceptable salt thereof; wherein $Xaa_1$ is Asn, D-Asn, Gln, D-Gln, Pro, Ala, β-Ala, D-Ala, Val, D-Val, Gly, Thr, D-Thr, Asp, D-Asp, γ-carboxylated Asp, Glu, D-Glu, γ-carboxylated Glu, α-aminosuberic acid (Asu), α-aminoadipic acid (Aad), α-aminopimelic acid (Apm), or is absent;

$Xaa_2$ is Asp, γ-carboxylated Asp, Glu, γ-carboxylated Glu, Asu, Aad, Apm, or is absent;

$Xaa_3$ is Asp, γ-carboxylated Asp, Glu, γ-carboxylated Glu, Asu, Aad, Apm, or is absent;

$Xaa_4$ is Cys or D-Cys;

$Xaa_6$ is P-Ser, P-Thr, P-homo-Ser, 4-hydroxyvaline phosphate, P-homo-Thr, P-Cys or P-Tyr;

$Xaa_7$ is Tyr, Leu, Phe or Ile;

$Xaa_8$ is Cys or D-Cys;

$Xaa_{14}$ is Thr, Ala or Phe;

$Xaa_{16}$ is Cys or D-Cys; and $Xaa_{17}$ is Tyr, D-Tyr, or is absent;

wherein:

if $Xaa_1$ is present, $Xaa_1$ may be modified on its amino group by methyl, ethanedioic acid, propanedioic acid, butanedioic acid, pentanedioic acid, hexanedioic acid, heptanedioic acid or octanedioic acid;

if $Xaa_1$ is absent and $Xaa_2$ is present, then $Xaa_2$ may be modified on its amino group by methyl, ethanedioic acid, propanedioic acid, butanedioic acid, pentanedioic acid, hexanedioic acid, heptanedioic acid or octanedioic acid; or if both $Xaa_1$ and $Xaa_2$ are absent, then $Xaa_3$ may be modified on its amino group by methyl, ethanedioic acid, propanedioic acid, butanedioic acid, pentanedioic acid, hexanedioic acid, heptanedioic acid or octanedioic acid.

In some embodiments, both $Xaa_2$ and $Xaa_3$ are absent. In other embodiments, $Xaa_2$ is Asp or Glu and $Xaa_3$ is absent. In yet other embodiments, wherein $Xaa_2$ is Asp or Glu and $Xaa_3$ is Asp or Glu.

In some embodiments, $Xaa_7$ is Tyr or Leu.

In some embodiments, $Xaa_{14}$ is Thr.

In some embodiments, $Xaa_{17}$ is Tyr or is absent.

In some embodiments, $Xaa_1$ is Asn, D-Asn, Gln, D-Gln, Pro, Ala, β-Ala, D-Ala, Val, D-Val, Gly, Thr, D-Thr, Asp, D-Asp, Glu or D-Glu. In further embodiments, $Xaa_1$ is Asp, D-Asp, Glu or D-Glu.

In some embodiments, $Xaa_6$ is P-Ser or P-Thr. In further embodiments, $Xaa_6$ is P-Ser.

In some embodiments, $Xaa_1$, $Xaa_2$ and $Xaa_3$ are absent and $Xaa_4$ is D-Cys or Cys. In further embodiments, $Xaa_7$ is Tyr or Leu. In further embodiments, $Xaa_{14}$ is Thr. In further embodiments, $Xaa_{17}$ is Tyr or is absent. In further embodiments, $Xaa_6$ is P-Ser.

In some embodiments, a peptide or pharmaceutically acceptable salt thereof is provided that is useful for the treatment of lower GI disorders, in particular disorders such as IBS-C and CC, wherein the peptide consists of the amino acid sequence $Cys_4$ $Cys_5$ $P\text{-}Ser_6$ $Xaa_7$ $Cys_8$ $Cys_9$ $Asn_{10}$ $Pro_{11}$ $Ala_{12}$ $Cys_{13}$ $Thr_{14}$ $Gly_{15}$ $Cys_{16}$ $Xaa_{17}$, wherein $Xaa_7$ is Tyr or Leu and $Xaa_{17}$ is Tyr or is absent [SEQ ID No: 10].

In some embodiments, a peptide or pharmaceutically acceptable salt thereof is provided that is useful for the treatment of lower GI disorders, in particular disorders such as IBS-C and CC, wherein the peptide consists of the amino acid sequence

[SEQ ID No: 2]
Asp Asp Cys Cys P-Ser Leu Cys Cys Asn Pro Ala Cys
Thr Gly Cys Tyr;

[SEQ ID No: 3]
Asp Asp Cys Cys P-Ser Leu Cys Cys Asn Pro Ala Cys
Thr Gly Cys;

[SEQ ID No: 4]
Asp Asp Cys Cys P-Ser Tyr Cys Cys Asn Pro Ala Cys
Thr Gly Cys Tyr;

[SEQ ID No: 5]
Asp Asp Cys Cys P-Ser Tyr Cys Cys Asn Pro Ala Cys
Thr Gly Cys;

[SEQ ID No: 6]
Cys Cys P-Ser Leu Cys Cys Asn Pro Ala Cys Thr Gly
Cys Tyr;

[SEQ ID No: 7]
Cys Cys P-Ser Leu Cys Cys Asn Pro Ala Cys Thr Gly
Cys;

[SEQ ID No: 8]
Cys Cys P-Ser Tyr Cys Cys Asn Pro Ala Cys Thr Gly
Cys Tyr;
or

[SEQ ID No: 9]
Cys Cys P-Ser Tyr Cys Cys Asn Pro Ala Cys Thr Gly
Cys.

In some instances, the peptide is isolated. In others, the peptide is purified.

In some embodiments, $Xaa_6$ is any amino acid that may be phosphorylated.

In some embodiments, a pharmaceutically acceptable salt of the peptide is provided. In some instances, the pharmaceutically acceptable salt is a chloride salt.

Variant Peptides

In some circumstances it may be desirable to use a variant peptide or pharmaceutically acceptable salt that binds to and activates intestinal GC-C receptors, but is less active or more active than the non-variant form of the peptide in the pharmaceutical compositions, uses and methods described herein. Reduced activity can arise from reduced affinity for the receptor or a reduced ability to activate the receptor once bound or reduced stability of the peptide. Increased activity can arise from increased affinity for the receptor or an increased ability to activate the receptor once bound or increased stability of the peptide.

In some peptides one or both members of one or both pairs of Cys residues which normally form a disulfide bond can be replaced by homocysteine, penicillamine, 3-mercaptoproline (Kolodziej et al. 1996 *Int J Pept Protein Res* 48:274); β,β-dimethylcysteine (Hunt et al. 1993 *Int J Pept Protein Res* 42:249) or diaminopropionic acid (Smith et al. 1978 *J Med Chem* 21:117) to form alternative internal cross-links at the positions of the normal disulfide bonds. In other embodiments, the disulfide bonds may be replaced by hydrocarbon crosslinking (Schafmeister et al. 2000 J Am Chem Soc 122:5891, Patgiri et al. 2008 Acc Chem Res 41:1289, Henchey et al. 2008 Curr Opin Chem Biol 12:692).

Production of Peptides

In one embodiment, peptides or precursor peptides to be used in the pharmaceutical compositions and methods described herein can be produced recombinantly in any known protein expression system, including, without limitation, bacteria (e.g., *E. coli* or *Bacillus subtilis*), insect cell systems (e.g., *Drosophila* Sf9 cell systems), yeast cell systems (e.g., *S. cerevisiae, S. saccharomyces*) or filamentous fungal expression systems, or animal cell expression systems (e.g., mammalian cell expression systems). Peptides or precursor peptides of the invention may also be chemically synthesized.

If the peptide or variant peptide is to be produced recombinantly, e.g., *E. coli*, the nucleic acid molecule encoding the peptide may also encode a leader sequence that permits the secretion of the mature peptide from the cell. Thus, the sequence encoding the peptide can include the pre sequence and the pro sequence of, for example, a naturally-occurring bacterial ST peptide. The secreted, mature peptide can be purified from the culture medium.

The sequence encoding a peptide described herein is can be inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or M13 and derivatives thereof. Construction of a vector containing a nucleic acid described herein can be followed by transformation of a host cell such as a bacterium. Suitable bacterial hosts include but are not limited to, *E. coli, B. subtilis, Pseudomonas* and *Salmonella*. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during peptide production.

The protein coding sequence that includes a peptide described herein can also be fused to a nucleic acid encoding a peptide affinity tag, e.g., glutathione S-transferase (GST), maltose E binding protein, protein A, FLAG tag, hexa-histidine, myc tag or the influenza HA tag, in order to facilitate purification. The affinity tag or reporter fusion joins the reading frame of the peptide of interest to the reading frame of the gene encoding the affinity tag such that a translational fusion is generated. Expression of the fusion gene results in translation of a single peptide that includes both the peptide of interest and the affinity tag. In some instances where affinity tags are utilized, DNA sequence encoding a protease recognition site will be fused between the reading frames for the affinity tag and the peptide of interest.

Genetic constructs and methods suitable for production of immature and mature forms of the peptides and variants described herein in protein expression systems other than bacteria, and well known to those skilled in the art, can also be used to produce peptides in a biological system.

Peptides produced recombinantly may be phosphorylated using methods known to those skilled in the art. In some embodiments, a peptide is recombinantly produced, isolated from the cell in which it was expressed, and then phosphorylated using a protein kinase, e.g., a serine/threonine kinase or a tyrosine kinase. A large number of kinases are known in the art and may be used for this purpose. One skilled in the art will recognize that different kinases have differing substrate specificities and will pick a kinase to use based upon the sequence of the peptide. In other embodiments, a peptide is recombinantly produced in a cell that also expresses a serine/threonine kinase or tyrosine kinase that will phosphorylate the peptide. In other embodiments, peptides may be recombinantly produced by incorporating a phosphoamino acid. Methods for modifying tRNA including, but not limited to, modifying the anti-codon, the amino acid attachment site, and/or the accepter stem to allow incorporation of unnatural and/or arbitrary amino acids are known in the art (Biochem. Biophys. Res. Comm. (2008) 372: 480-485; Chem. Biol. (2009) 16:323-36; Nat. Methods (2007) 4:239-44; Nat. Rev. Mol. Cell Biol. (2006) 7:775-82; Methods (2005) 36:227-238; Methods (2005) 36:270-278; Annu. Rev. Biochem. (2004) 73:147-176; Nuc. Acids Res. (2004) 32:6200-6211; Proc. Natl. Acad. Sci. USA (2003) 100:6353-6357; Royal Soc. Chem. (2004) 33:422-430).

In some embodiments, peptides may be chemically produced. Peptides can be synthesized by a number of different methods including solution and solid phase synthesis using traditional BOC or FMOC protection. For example, the peptide can be synthesized on 2-Chlorotritylchloride or Wang resin using consecutive amino acid couplings. The following protecting groups can be used: Fluorenylmethyloxycarbonyl or tert-butyloxycarbonyl (alpha-amino groups, N-terminus); trityl or tert-butyl (thiol groups of Cy); tert-butyl (γ-carboxyl of glutamic acid and the hydroxyl group of threonine, if present); trityl (β-amid function of the asparagine side chain and the phenolic group of tyrosine, if present); trityl or tert-butyldimethylsilyl (hydroxygroup of serine, if present) and tert-Butyloxycarbonyl (N-terminus prior to subsequent side chain modifications). Coupling can be effected with DIC and HOBt in the presence of a tertiary amine, and the peptide can be deprotected and cleaved from the solid support in using cocktail K (trifluoroacetic acid 81%, phenol 5%, thioanisole 5%, 1,2-ethanedithiol 2.5%, water 3%, dimethylsulphide 2%, ammonium iodide 1.5% w/w). After removal of trifluoroacetic acid and other volatiles the peptide can be precipitated using an organic solvent. Disulfide bonds between Cys residues can be formed using dimethyl sulfoxide (Tam et al. (1991) J. Am. Chem. Soc. 113:6657-62) or using an air oxidation strategy. The resulting peptide can be purified by reverse-phase chromatography and lyophilized.

A phosphoamino acid, e.g., a phosphoserine, may be introduced into a peptide by any method known to one skilled in the art (see, e.g., G. K. Toth et al. (2007), Current Organic Chemistry 11: 409-426). In some embodiments, a protected phosphoamino acid analogue, e.g., a phosphoserine amino acid analogue, can be introduced as part of the peptide assembly on solid phase; e.g. as Fmoc-Ser[PO(OBzl)OH]-OH (T. Wakamiya et al. (1997), Bioorganic and Medicinal Chemistry 5: 135-145, 1997) or as Fmoc-Ser[PO(OAryl/Alkyl)$_2$]-OH (G. K. Toth et al. (2007) Current Organic Chemistry, 11: 409-426). In another embodiment, a protected amino acid analogue, e.g., a protected serine amino acid analogue, can be introduced as part of the peptide assembly on solid phase (e.g. Fmoc-protected serine with a trityl protection for the hydroxyl side chain). After full assembly of the peptide chain Ser[Trt] or Ser[SiMe$_2$tBu] can be selectively deprotected and the phosphate group can be introduced using a phosphoramidite/oxidation strategy (G. Shapiro et al. (1994) Tetrahedron Letters 35: 869-872; P. Hormozdiari et al. (1996) Tetrahedron Letters, 37: 8227-8230). In other embodiments, a chemically produced peptide may be phosphorylated using a serine/threonine kinase or tyrosine kinase as described above.

Peptides can be made, isolated or used either in form of the free base or as pharmaceutically acceptable salts thereof. Examples of salts include, without limitation, acetate, chloride, sulfate and phosphate salts of the peptide.

Compositions of Peptides and GC-C Receptor Agonists

In another aspect, compositions are provided wherein the peptides, alone or in combination, can be combined with any pharmaceutically acceptable carrier or medium. The peptides can be combined with materials that do not produce an adverse, allergic or otherwise unwanted reaction when administered to a patient. The carriers or mediums used can include solvents, dispersants, coatings, absorption promoting agents, controlled release agents, and one or more inert excipients (which include starches, polyols, granulating agents, microcrystalline cellulose (e.g., celphere, Celphere Beads®), diluents, lubricants, binders, disintegrating agents, and the like), etc. If desired, tablet dosages of the disclosed compositions may be coated by standard aqueous or non-aqueous techniques.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

As used herein, the term "binder" refers to any pharmaceutically acceptable binder that may be used in the practice of the invention. Examples of pharmaceutically acceptable binders include, without limitation, a starch (e.g., corn starch, potato starch and pre-gelatinized starch (e.g., STARCH 1500® and STARCH 1500 LM®, sold by Colorcon, Ltd.) and other starches), maltodextrin, gelatin, natural and synthetic gums such as acacia, powdered tragacanth, guar gum, cellulose and its derivatives (e.g., methylcellulose, hydroxyethyl cellulose, hydroxyethyl methylcellulose, hydroxypropyl cellulose and hydroxypropyl methylcellulose (hypromellose), ethyl cellulose, cellulose acetate, carboxymethyl cellulose calcium, sodium carboxymethyl cellulose, carboxymethylcellulose, powdered cellulose, microfine cellulose, microcrystalline cellulose (e.g. AVICEL™, such as, AVICEL-PH-101™, -103™ and -105™, sold by FMC Corporation, Marcus Hook, Pa., USA)), polyvinyl alcohol, polyvinyl pyrrolidone (e.g., polyvinyl pyrrolidone K30), and mixtures thereof.

Examples of binders that may be particularly used in pharmaceutical compositions include polyvinyl alcohol, polyvinylpyrrolidone (povidone), a starch, maltodextrin or a cellulose ether (such as, for example, methylcellulose, ethylcellulose, carboxymethylcellulose, hydroxyethyl cellulose, hydroxyethyl methylcellulose, hydroxypropyl cellulose and hydroxypropyl methylcellulose).

As used herein, the term "filler" refers to any pharmaceutically acceptable filler that may be used in the practice of the invention. Examples of pharmaceutically acceptable fillers include, without limitation, talc, calcium carbonate (e.g., granules or powder), dibasic calcium phosphate, tribasic calcium phosphate, calcium sulfate (e.g., granules or powder), microcrystalline cellulose (e.g., Avicel PH101 or Celphere CP-305), microfine cellulose, powdered cellulose, dextrates, kaolin, mannitol, silicic acid, sorbitol, starch (e.g., Starch 1500), pre-gelatinized starch, lactose, glucose, fructose, galactose, trehalose, sucrose, maltose, isomalt, raffinose, maltitol, melezitose, stachyose, lactitol, palatinite, xylitol, myoinositol, and mixtures thereof.

Examples of pharmaceutically acceptable fillers that may be particularly used for coating the peptides include, without limitation, talc, microcrystalline cellulose (e.g., Avicel PH101 or Celphere CP-305), powdered cellulose, dextrates, kaolin, mannitol, silicic acid, sorbitol, starch, pre-gelatinized starch, lactose, glucose, fructose, galactose, trehalose, sucrose, maltose, isomalt, dibasic calcium phosphate, raffinose, maltitol, melezitose, stachyose, lactitol, palatinite, xylitol, mannitol, myoinositol, and mixtures thereof.

As used herein, the term "additives" refers to any pharmaceutically acceptable additive. Pharmaceutically acceptable additives include, without limitation, disintegrants, dispersing additives, lubricants, glidants, antioxidants, coating additives, diluents, surfactants, flavoring additives, humectants, absorption promoting additives, controlled release additives, anti-caking additives, anti-microbial agents (e.g., preservatives), colorants, desiccants, plasticizers and dyes. As used herein, an "excipient" is any pharmaceutically acceptable additive, filler, binder or agent.

Compositions may also optionally include other therapeutic ingredients, anti-caking agents, preservatives, sweetening agents, colorants, flavors, desiccants, plasticizers, dyes, glidants, anti-adherents, anti-static agents, surfactants (wetting agents), anti-oxidants, film-coating agents, and the like. Any such optional ingredient must be compatible with the compound described herein to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

The compositions can include, for example, various additional solvents, dispersants, coatings, absorption promoting additives, controlled release additives, and one or more inert additives (which include, for example, starches, polyols, granulating additives, microcrystalline cellulose, diluents, lubricants, binders, disintegrating additives, and the like), etc. If desired, tablet dosages of the disclosed compositions may be coated by standard aqueous or non-aqueous techniques. Compositions can also include, for example, anti-caking additives, preservatives, sweetening additives, colorants, flavors, desiccants, plasticizers, dyes, and the like.

Suitable disintegrants include, for example, agar-agar, calcium carbonate, microcrystalline cellulose, croscarmellose sodium, crospovidone, povidone, polacrilin potassium, sodium starch glycolate, potato or tapioca starch, other starches, pre-gelatinized starch, clays, other algins, other celluloses, gums, and mixtures thereof.

Suitable lubricants include, for example, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Evonik Degussa Co., Plano, Tex. USA), a pyrogenic silicon dioxide (CAB-O-SIL, Cabot Co., Boston, Mass. USA), and mixtures thereof.

Suitable glidants include, for example, leucine, colloidal silicon dioxide, magnesium trisilicate, powdered cellulose, starch, talc, and tribasic calcium phosphate.

Suitable anti-caking additives include, for example, calcium silicate, magnesium silicate, silicon dioxide, colloidal silicon dioxide, talc, and mixtures thereof.

Suitable anti-microbial additives that may be used, e.g., as a preservative for the peptides compositions, include, for example, benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, and mixtures thereof.

Suitable antioxidants include, for example, BHA (butylated hydroxyanisole), BHT (butylated hydroxytoluene), vitamin E, propyl gallate, ascorbic acid and salts or esters thereof, tocopherol and esters thereof, alpha-lipoic acid and beta-carotene.

Suitable coating additives include, for example, sodium carboxymethyl cellulose, cellulose acetate phthalate, ethylcellulose, gelatin, pharmaceutical glaze, hydroxypropyl cellulose, hydroxypropyl methylcellulose, hydroxypropyl methyl cellulose phthalate, methylcellulose, polyethylene glycol, polyvinyl acetate phthalate, shellac, sucrose, titanium dioxide, carnauba wax, microcrystalline wax, and mixtures thereof. Suitable protective coatings include Aquacoat (e.g., Aquacoat Ethylcellulose Aquaeous Dispersion, 15% w/w, FMC Biopolymer, ECD-30), Eudragit (e.g., Eudragit E PO PE-EL, Roehm Pharma Polymers) and Opadry (e.g Opadry AMB dispersion, 20% w/w, Colorcon).

In certain embodiments, suitable additives for the peptides composition include one or more of sucrose, talc, magnesium stearate, crospovidone or BHA.

The compositions of the present invention can also include other excipients, agents, and categories thereof including but not limited to L-histidine, PluronicID, Poloxamers (such as Lutrol® and Poloxamer 188), ascorbic acid, glutathione, permeability enhancers (e.g., lipids, sodium cholate, acylcarnitine, salicylates, mixed bile salts, fatty acid micelles, chelators, fatty acid, surfactants, medium chain glycerides), protease inhibitors (e.g., soybean trypsin inhibitor, organic acids), pH lowering agents and absorption enhancers effective to promote bioavailability (including but not limited to those described in U.S. Pat. No. 6,086,918 and U.S. Pat. No. 5,912,014), materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); soft gelatin capsules (like sorbitol special solution); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD& C Yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, mannitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

In some embodiments, there is provided a pharmaceutical composition that is useful for the treatment of lower GI disorders, in particular disorders such as IBS-C and CC. In some embodiments, the pharmaceutical composition comprises a peptide or pharmaceutically acceptable salt thereof as described herein and one or more stabilizing agents selected from $Mg^{2+}$, $Ca^{2+}$, $Zn^{2+}$, $Mn^{2+}$, $K^+$, $Na^+$ or $Al^{3+}$, a combination thereof, and/or a sterically hindered primary amine. In further embodiments, the agent is $Mg^{2+}$, $Ca^{2+}$ or $Zn^{2+}$ or a combination thereof In some embodiments, the cation is provided, without limitation, as magnesium acetate, magnesium chloride, magnesium phosphate, magnesium sulfate, calcium acetate, calcium chloride, calcium phosphate, calcium sulfate, zinc acetate, zinc chloride, zinc phosphate, zinc sulfate, manganese acetate, manganese chloride, manganese phosphate, manganese sulfate, potassium acetate, potassium chloride, potassium phosphate, potassium sulfate, sodium acetate, sodium chloride, sodium phosphate, sodium sulfate, aluminum acetate, aluminum chloride, aluminum phosphate or aluminum sulfate. In further embodiments, the cation is provided as magnesium chloride, calcium chloride, calcium phosphate, calcium sulfate, zinc acetate, manganese chloride, potassium chloride, sodium chloride or aluminum chloride. In other embodiments, the cation is provided as calcium chloride, magnesium chloride or zinc acetate.

In another embodiment, the stabilizing agent is a sterically hindered primary amine. In a further embodiment, the sterically hindered primary amine is an amino acid. In yet a further embodiment, the amino acid is a naturally-occurring amino acid. In a still further embodiment, the naturally-occurring amino acid is selected from the group consisting of: histidine, phenylalanine, alanine, glutamic acid, aspartic acid, glutamine, leucine, methionine, asparagine, tyrosine, threonine, isoleucine, tryptophan, glycine and valine; yet further, the naturally-occurring amino acid is leucine, isoleucine, alanine or methionine. In another embodiment, the sterically hindered primary amine is a non-naturally occurring amino acid (e.g., 1-aminocyclohexane carboxylic acid). In a further embodiment, the sterically hindered primary amine is cyclohexylamine, 2-methylbutylamine or a polymeric amine such as chitosan. In another embodiment, one or more sterically hindered primary amines may be used in a composition.

In some cases, the sterically hindered primary amine has the formula:

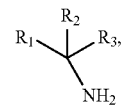

wherein $R_1$, $R_2$ and $R_3$ are independently selected from: H, C(O)OH, $C_1$-$C_6$ alkyl, $C_1$-$C_6$ alkylether, $C_1$-$C_6$ alkylthioether, $C_1$-$C_6$ alkyl carboxylic acid, $C_1$-$C_6$ alkyl carboxylamide and alkylaryl, wherein any group can be singly or multiply substituted with: halogen or amino, and provided that no more than two of $R_1$, $R_2$ and $R_3$ are H. In another embodiment, no more than one of $R_1$, $R_2$ and $R_3$ is H.

In other embodiments, there is provided a pharmaceutical composition comprising a pharmaceutically acceptable carrier, peptide, a cation selected from $Mg^{2+}$, $Ca^{2+}$, $Zn^{2+}$, $Mn^{2+}$, $K^+$, $Na^+$ or $Al^{3+}$, or a mixture thereof, and a sterically hindered primary amine. In one embodiment, the cation is $Mg^{2+}$, $Ca^{2+}$ or $Zn^{2+}$ or a mixture thereof. In a further embodiment, the pharmaceutical composition further comprises a pharmaceutically acceptable binder and/or a pharmaceutically acceptable glidant, lubricant or additive that acts as both a glidant and lubricant and/or an antioxidant. In some embodiments, the pharmaceutical composition is applied to a carrier. In some embodiments, the carrier is a filler.

In some cases the molar ratio of cation:sterically hindered primary amine: peptide in the aqueous solution applied to the carrier is 5-100:5-50:1. In some cases, the molar ratio of cation:sterically hindered primary amine may be equal to or greater than 2:1 (e.g., between 5:1 and 2:1). Thus, in some cases the molar ratio of cation:sterically hindered primary amine: peptide applied to the carrier is 100:50:1, 100:30:1, 80:40:1, 80:30:1, 80:20:1, 60:30:1, 60:20:1, 50:30:1, 50:20:1, 40:20:1, 20:20:1, 10:10:1, 10:5:1 or 5:10:1. When binder, e.g., methylcellulose, is present in the GC-C agonist peptide solution applied to the carrier it can be present at 0.5%-2.5% by weight (e.g., 0.7%-1.7% or 0.7%-1% or 1.5% or 0.7%).

It has been found that a cation selected from $Mg^{2+}$, $Ca^{2+}$, $Zn^{2+}$, $Mn^{2+}$, $K^+$, $Na^+$ and $Al^{3+}$ is useful for suppressing the formation of an oxidation product of GC-C receptor agonist polypeptides during storage. It has also been found that a sterically hindered primary amine is useful for suppressing the formation of a formaldehyde imidazolidinone adduct ("formaldehyde imidazolidinone product") of the GC-C receptor agonist polypeptides during storage. Thus, the GC-C receptor agonist polypeptide formulations comprising a cation selected from $Mg^{2+}$, $Ca^{2+}$, $Zn^{2+}$, $Mn^{2+}$, $K^+$, $Na^+$ or $Al^{3+}$—for example, a divalent cation selected from $Zn^{2+}$, $Mg^{2+}$ and $Ca^{2+}$—and/or a sterically hindered primary amine, such as an amino acid, have a sufficient shelf life (as measured by chromatographic purity and/or by a weight/weight assay) for manufacturing, storing and distributing the drug. Further, while the presence of a sterically hindered amine alone can increase the formation of a hydrolysis product of linaclotide during storage, the combination of a sterically hindered primary amine and a cation, e.g., but not limited to, the combination of leucine and $Ca^{2+}$, suppresses the formation of the hydrolysis product of the GC-C receptor agonist polypeptide as well as the oxidation product of GC-C receptor agonist polypeptide during storage, leading to an even greater overall stability as determined by a weight/weight assay and/or by chromatographic purity.

In a further embodiment, the pharmaceutical composition further comprises a pharmaceutically acceptable binder or additive, and/or a pharmaceutically acceptable glidant, lubricant or additive that acts as both a glidant and lubricant and/or an antioxidant.

Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well known in the art, as exemplified by Remington's Pharmaceutical Sciences (18th Edition, Mack Publishing Company, 1995).

For treatment of gastrointestinal disorders, the peptides described herein are preferably administered orally, e.g., as a tablet, capsule, sachet containing a predetermined amount of the active ingredient pellet, gel, paste, syrup, bolus, electuary, slurry, powder, lyophilized powder, granules, as a solution or a suspension in an aqueous liquid or a non-aqueous liquid; as an oil-in-water liquid emulsion or a water-in-oil liquid emulsion, via a liposomal formulation (see, e.g., EP 736299) or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein. The peptides can be co-administered with other agents used to treat gastrointestinal disorders including but not limited to the agents described herein.

In another aspect, suitable pharmaceutical compositions may comprise one or more other therapeutic agents. Such therapeutic agents include, without limitation, analgesic agents; anti-secretory agents, including proton pump inhibitors, acid pump antagonists, H2 receptor antagonists; PDE5 inhibitors; GABA-B antagonists; bile acid sequestrants; prokinetic and promotility agents; antidepressants; antibiotics; antiemetics; and mucosal-protecting agents.

Methods of Treatment

In certain embodiments of the invention, a method of treatment is provided for a lower GI disorder.

Compositions containing one or more GC-C agonist peptides described herein can be used to treat a variety of lower GI disorders. In certain embodiments, the lower GI disorder is selected from impaired lower intestinal mobility, irritable bowel syndrome (e.g., IBS-C and mixed irritable bowel syndrome (IBS-M)), constipation (e.g., chronic constipation), intestinal or colonic pseudo-obstruction, functional bloating, and post-operative ileus.

In certain embodiments, compositions containing one or more GC-C agonist peptides described herein can be used alone or in combination therapy for the treatment, prevention or reduction of visceral or abdominal pain associated with a GI disorder, such as a GI disorder described herein, or pain associated with another disorder. In some embodiment, the peptides are useful for ameliorating abdominal pain and/or discomfort associated with CC or IBS-C.

In another aspect, there is provided a GC-C agonist peptide as described herein that may be used in the manufacture of a medicament for the treatment of a lower GI disorder. In various embodiments, the lower GI disorder is selected from impaired lower intestinal mobility, irritable bowel syndrome (e.g., IBS-C and mixed irritable bowel syndrome (IBS-M)), constipation (e.g., chronic constipation), intestinal or colonic pseudo-obstruction, functional bloating, and post-operative ileus. In another aspect, there is provided a GC-C agonist peptide as described herein that may be used in the manufacture of a medicament for the treatment, prevention or reduction of visceral or abdominal pain associated with a GI disorder, such as a GI disorder described herein, or pain associated with another disorder. In some embodiments, there is provided a GC-C agonist peptide as described herein that may be used in the manufacture of a medicament for ameliorating abdominal pain and/or discomfort associated with CC or IBS-C.

In some embodiments, the GC-C agonist peptides described herein can be used to treat and/or prevent constipation. Constipation can be used to describe bowel patterns which include one or more of hard, small, infrequent stools;

the sensation of difficulty in passing stool, specifically excessive or ineffectual straining; the sensation of incomplete evacuation. Constipation has also been described as the passage of stool less than a certain number (e.g. 3) of times per week.

Constipation can be associated with numerous disorders and conditions. For example, constipation can be (1) associated with the use of a therapeutic agent (e.g. antihypertensives, anticonvulsants, antispasmodics, analgesics, anticholinergics, antidepressants, antipsychotics, cation-containing agents, anticonvulsants, ganglion blockers, vinca alkaloids); (2) associated with a muscular, neuropathic, metabolic or endocrine disorder (including but not limited to myotonic dystrophy, dermamyositis, systemic sclerosis, sclerodoma, amyloidosis (neurologic or muscular), ischemia, tumor of the central nervous system, autonomic neuropathy, Chagas disease, cystic fibrosis, diabetes mellitus, Hirschsprung disease, hyperthyroidism, hypocalcaemia, hypothyroidism, Multiple Sclerosis, neurofibromatosis, Parkinson's disease, and spinal cord lesions (for example, related to sacral nerve damage related to trauma or a tumor or the enteric nervous system)); (3) post-surgical constipation (postoperative ileus); (4) associated with a structural colon alteration (for example that associated with Neoplasm, stricture, volvulus, anorectal, inflammation, prolapse, rectocele, or fissure); (5) associated with a GI disorder; (6) associated with a systemic illness or disorder (for example, electrolyte abnormalities, thyroid disease, diabetes mellitus, panhypopituitarism, Addison's disease, pheochromocytoma, uremia, porphyria); (7) chronic constipation; (8) associated with the use of analgesic drugs (e.g. opioid-induced constipation), antihypertensives, anticonvulsants, antidepressants, antispasmodics and antipsychotics; (9) associated with megacolon; and (10) idiopathic constipation (functional constipation).

Functional constipation can be associated with normal transit, slow transit (e.g. one or fewer bowel movements per week) and pelvic floor dyssynergia. Pelvic floor dyssynergia is considered a disorder of the rectum and anus although these patients also have abnormal contractions throughout the colon. Patients with pelvic floor dyssynergia have abnormal colonic pressure waves prior to defecation and present with symptoms that may include a sensation of incomplete evacuation, excessive straining, a need for digital disimpaction, perianal heaviness, and tenesmus. Constipation can be associated with bloating and abdominal pain. The peptides and agonists described herein can be used to prevent and/or treat low stool frequency or poor stool consistency.

In some embodiments, there are provided methods for treating irritable bowel syndrome with constipation (IBS-C) in a patient in need thereof, comprising administering to the patient once daily an effective amount of a pharmaceutical composition comprising one or more GC-C agonist peptides as described herein. In various embodiments, the pharmaceutical composition comprises 50 µg to 1 mg peptide per unit dose per day. In other embodiments, the pharmaceutical composition is administered for a period of at least one day, two days, three days, four days, five days, six days, one week, two weeks, three weeks, four weeks, eight weeks, nine weeks, twelve weeks or longer. In some embodiments, treatment with the composition improves at least one symptom selected from reduced abdominal pain, an increase in the number of complete spontaneous bowel movements (CSBM) in a week, an increase in the number of spontaneous bowel movements (SBM) in a week, improved stool consistency, reduced straining, reduced abdominal discomfort, reduced bloating or reduced IBS-C symptom severity.

In some embodiments, there are provided methods for treating chronic constipation in a patient in need thereof, comprising administering to the patient once daily an effective amount of a pharmaceutical composition comprising one or more GC-C agonist peptides as described herein. In various embodiments, the pharmaceutical composition comprises 50 µg to 1 mg peptide per unit dose per day. In other embodiments, the pharmaceutical composition is administered for a period of at least one day, two days, three days, four days, five days, six days, one week, two weeks, three weeks, four weeks, eight weeks, nine weeks, twelve weeks, or longer. In some embodiments, treatment with the composition improves at least one symptom selected from an increase in the number of complete spontaneous bowel movements (CSBM) in a week, an increase in the number of spontaneous bowel movements (SBM) in a week, improved stool consistency, reduced straining, reduced abdominal discomfort, reduced bloating or reduced severity of constipation.

Stool consistency of each BM may be monitored by the 7-point Bristol Stool Form Scale (BSFS) (1=hard lumps, 2=lumpy sausage, 3=cracked sausage, 4=smooth sausage, 5=soft lumps, 6=mushy, 7=watery). Straining may be monitored by the 7-point Ease of Passage Scale (1=manual disimpaction/enema needed, 2=severe straining, 3=moderate straining, 4=mild straining, 5=no straining, 6=urgency, 7=incontinent). CSBM may be measured by the sensation of complete emptying after an SBM (yes/no). Abdominal discomfort, bloating and severity of constipation may be measured using, e.g., a 5-point ordinal scale (1=none, 2=mild, 3=moderate, 4=severe, 5=very severe).

The peptides and agonists described herein can be used alone or in combination therapy for the treatment, prevention or reduction of visceral pain associated with a lower gastrointestinal disorder or pain associated with another disorder as described herein.

The peptides described herein can be administered in combination with other agents for the treatment of lower GI disorders, such as IBS-C and CC. For example, the peptides can be administered with an analgesic peptide or compound. The analgesic peptide or compound can be covalently attached to a peptide described herein or it can be a separate agent that is administered together with or sequentially with a peptide described herein in a combination therapy. The GC-C receptor agonists described herein may also be administered in combination with other agents used to treat lower GI disorders including antidepressants, promotility or prokinetic agents, antiemetics, antibiotics, proton pump inhibitors, acid blockers (e.g., histamine H2 receptor antagonists), acid pump antagonists, PDE5 inhibitors, GABA-B agonists, bile acid sequestrants, and mucosal protecting agents.

In some embodiments, useful analgesic agents that may be used with the peptides described herein include Ca channel blockers (e.g., ziconotide), 5HT receptor antagonists (e.g., 5HT3, 5HT4 and 5HT1 receptor antagonists), 5HT4 agonists (e.g., tegaserod (Zelnorm®), mosapride, metoclopramide, zacopride, cisapride, renzapride, benzimidazolone derivatives such as BIMU 1 and BIMU 8, and lirexapride), 5HT1 agonists (e.g., sumatriptan and buspirone), opioid receptor agonists (e.g., loperamide, fedotozine, enkephalin pentapeptide, morphine, diphenyloxylate, frakefamide, trimebutine and fentanyl), CCK receptor agonists (e.g., loxiglumide and dexloxiglumide), NK1 receptor antagonists (e.g., aprepitant, vofopitant, ezlopitant, R-673 (Hoffmann-La Roche Ltd), SR-48968 and SR-14033, (Sanofi Synthelabo), CP-122,721 (Pfizer, Inc.), GW679769 (Glaxo Smith Kline) and TAK-637 (Takeda/Abbot)), NK2 receptor antagonists (e.g., nepadutant, saredutant, GW597599 (Glaxo Smith Kline), SR-144190 (Sanofi-Synthelabo) and UK-290795 (Pfizer Inc)), NK3 receptor antagonists (e.g., osanetant (SR-142801; Sanofi-Synthelabo), SR-241586 and talnetant), norepinephrine-serotonin reuptake inhibitors (NSRI) (e.g., milnacipran), vanilloid and cannabanoid receptor agonists, sialorphin and sialorphin-related peptides. Analgesic agents in the various classes are described in the literature.

In some embodiments, one or more other therapeutic agents may be used in combination with the peptides described herein. Such agents include antidepressants, promotility or prokinetic agents, antiemetics, antibiotics, proton pump inhibitors, acid blockers (e.g., histamine H2 receptor antagonists), acid pump antagonists, PDE5 inhibitors, GABA-B agonists, bile acid sequestrants, and mucosal protecting agents.

Examples of antidepressants include, without limitation, tricyclic antidepressants such as amitriptyline (Elavil®), desipramine (Norpramin®), imipramine (Tofranil®), amoxapine (Asendin®), nortriptyline; the selective serotonin reuptake inhibitors (SSRI's) such as paroxetine (Paxil®), fluoxetine (Prozac®), sertraline (Zoloft®), and citralopram (Celexa®); and others such as doxepin (Sinequan®) and trazodone (Desyrel®).

Examples of promotility and prokinetic agents include, without limitation, itopride, octreotide, bethanechol, metoclopramide (Reglan®), domperidone (Motilium®), erythromycin (and derivatives thereof) and cisapride (Propulsid®). An example of antiemetics includes, without limitation, prochlorperazine.

Examples of antibiotics that may be used include those that may be used to treat *Heliobacter pylori* infections, such as amoxicillin, tetracycline, metronidazole, or clarithromycin. Other antibiotics such as erythromycin and derivatives thereof may also be used in combination with the peptides described herein.

Examples of proton pump inhibitors include, without limitation, omeprazole (Prilosec®), esomeprazole (Nexium®), lansoprazole (Prevacid®), pantoprazole (Protonix®) and rabeprazole (Aciphex®)). Examples of H2 receptor blockers include, without limitation, including cimetidine, ranitidine, famotidine and nizatidine. Examples of acid pump antagonists include, without limitation, revaprazan, CS-526 (J. Pharmacol. Exp. Ther. (2007) 323: 308-317), PF-03716556 (J. Pharmacol. Exp. Ther. (2009) 328(2):671-9), and YH1885 (Drug Metab. Dispos. (2001) 29(1):54-9).

Examples of PDE5 inhibitors include, without limitation, avanafil, lodenafil, mirodenafil, sildenafil citrate, tadalafil, vardenafil and udenafil. GABA-B agonists include, without limitation, baclofen and XP19986 (CAS Registry No. 847353-30-4). Examples of bile acid sequestrants include, without limitation, GT102-279, cholestyramine, colesevelam, colesevelam hydrochloride, ursodeoxycholic acid, colestipol, colestilan, sevelamer, polydiallylamine cross-linked with epichlorohydrin, dialkylaminoalkyl derivatives of a cross-linked dextran, and N-(cycloalkyl)alkylamines. Examples of mucosal protecting agents include, without limitation, sucralfate (Carafate), teprenone, polaprezinc, cetraxate and bismuth subsalicyclate.

Combination therapy can be achieved by administering two or more agents, e.g., a GC-C receptor agonist described herein and another therapeutic peptide or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

Dosage

The pharmaceutical compositions and peptides of the invention are administered in therapeutically effective amounts. A therapeutically effective amount is an amount sufficient to treat and/or prevent any lower GI disorders including but not limited to impaired lower intestinal mobility, irritable bowel syndrome (e.g., chronic constipation), intestinal or colonic pseudo-obstruction, functional bloating, and post-operative ileus. In certain aspects of the invention a therapeutically effective amount is an amount sufficient to ameliorate or lessen any symptoms associated with lower GI disorders, including but not limited to visceral or abdominal pain, bloating, discomfort, stool consistency, straining and constipation severity.

The dose range for adult humans may be generally from 5 μg to 100 mg/day orally of the GC-C peptide agonist described herein. Tablets, capsules, or other forms of presentation provided in discrete units may conveniently contain an amount of compound described herein which is effective at such dosage or as a multiple of the same, for instance, units containing 25 μg to 2 mg or around 100 μg to 1 mg. The precise amount of compound prescribed to a patient will be the responsibility of the attendant physician. However, the dose employed will depend on a number of factors, including the age and sex of the patient, the precise disorder being treated, and its severity.

In various embodiments, the dosage unit is administered with food at any time of the day, without food at any time of the day, with food after an overnight fast (e.g. with breakfast), at bedtime after a low fat snack. In one particular embodiment, the dosage unit is administered prior to food consumption (e.g., before breakfast). In a further embodiment, the dosage unit is administered approximately 15 minutes to 1 hour prior to food consumption. In various embodiments, the dosage unit is administered once a day, twice a day, three times a day, four times a day, five times a day or six times a day. In certain embodiments the dosage unit and daily dose are equivalent. In certain embodiments, the dosage unit is administered once a day.

In combination therapy embodiments of the present invention, the precise amount of each of the two or more active ingredients in a dosage unit will depend on the desired dosage of each component. Thus, it can be useful to create a dosage unit that will, when administered according to a particular dosage schedule (e.g., a dosage schedule specifying a certain number of units and a particular timing for administration), deliver the same dosage of each component as would be administered if the patient was being treated with only a single component. In other circumstances, it might be desirable to create a dosage unit that will deliver a dosage of one or more components that is less than that which would be administered if the patient was being treated only with a single component. Finally, it might be desirable to create a dosage unit that will deliver a dosage of one or more components that is greater than that which would be administered if the patient was being treated only with a single component.

The pharmaceutical composition can include additional ingredients including but not limited to the active ingredients and excipients described herein. In certain embodiments, one or more therapeutic agents of the dosage unit may exist in an extended or control release formulation and additional therapeutic agents may not exist in extended release formulation. For example, a peptide or agonist described herein may exist in a controlled release formulation or extended release formulation in the same dosage unit with another agent that may or may not be in either a controlled release or extended release formulation. Thus, in certain embodiments, it may be desirable to provide for the immediate release of one or more of the agents described herein, and the controlled release of one or more other agents.

The present invention has been described with reference to certain exemplary embodiments thereof. However, it will be readily apparent to those skilled in the art that it is possible to embody the invention in specific forms other than those of the exemplary embodiments described above. This may be done without departing from the spirit of the invention. The exemplary embodiments are merely illustrative and should not be considered restrictive in any way. The scope of the invention is defined by the appended claims and their equivalents, rather than by the preceding description.

EXAMPLES

The GC-C agonist peptides or pharmaceutically acceptable salts thereof as described herein were prepared by solid phase chemical synthesis and natural folding (air oxidation) by American Peptide Company (Sunnyvale, Calif.). The peptides and their sequences are shown below (wherein the amino acid sequence is the standard one letter code and "pS" is phosphoserine):

| Peptide Name | Amino Acid Sequence |
| --- | --- |
| Peptide 1 | CCpSLCCNPACTGCY |
| Dephospho-Peptide 1 | CCSLCCNPACTGCY |
| Peptide 2 | CCpSLCCNPACTGC |
| Dephospho-Peptide 2 | CCSLCCNPACTGC |
| Peptide 3 | CCELCCNPACTGCY |
| Peptide 4 | CCEFCCNPACTGCY |
| Peptide 5 | DDCCpSLCCNPACTGCY |
| Peptide 6 | DDCCpSYCCNPACTGCY |

Example 1

Alkaline and Acid Phosphatase Effects on Peptide Substrates

For the alkaline phosphatase reactions, peptide stocks were prepared at 1 mg/mL in 0.1 M Tris-HCl pH 8, which were stored at −20° C. until assays were conducted. For the acid phosphatase reactions, peptide stocks were prepared at 1 mg/mL in 50 mM sodium phosphate pH 6, which was stored at −20° C. until assays were conducted.

Alkaline Phosphatase Reaction

Calf intestinal alkaline phosphatase (CIP) was obtained from New England BioLabs, Ipswich, Mass. Cat # MO290S. The CIP reaction solution was prepared by dilution with buffer (50 mM KCl, 10 mM Tris-HCl pH 8, 1 mM MgCl$_2$, 50% glycerol) to 0.5 units/μL. The alkaline phosphatase reaction solutions were assembled in 20 μL quantities containing:

2 μL 10×CIP buffer (1M NaCl, 500 mM Tris-HCl pH 8, 100 mM MgCl$_2$)
2 μL peptide stock (1 mg/mL)
12 μL H$_2$O
4 μL alkaline phosphatase (0, 0.5 or 2 units)

The reaction solutions were mixed gently and incubated for 90 minutes at 37° C. These reaction solutions were stored at −20° C. until analysis. For analysis, the reaction solutions were diluted from 7.5 μL of CIP treated peptide to 50 μL with 0.1% formic acid in water to a final concentration of 10 μM. The final solution of 20 μL was then analyzed by LCMS with conditions as shown in Table 1 below.

Control reactions were assembled for enzyme activity containing 10 mM p-nitrophenylphosphate in place of peptide. After incubation, the reactions were diluted with 0.1 mL of 100 mM borate buffer pH 9 and read at the absorbance of 405 nm to monitor p-nitrophenol appearance.

Acid Phosphatase Reactions

Potato acid phosphatase (PoAP) was obtained from Sigma, St. Louis, Miss. Cat #P1146 and human prostate acid phosphatase (HuPrAP) was obtained from MP Biochemicals, Solon, Ohio. Cat #153872. The acid phosphatases were dissolved to provide a solution containing 0.5 units AP/μL using 50 mM sodium acetate pH 5, 0.2 mM MgCl$_2$. The acid phosphatase reactions were assembled in 20 μL quantities containing:

2 μL 10× acid phosphatase buffer (500 mM sodium acetate pH 5, 2 mM MgCl$_2$)
2 μL peptide stock (1 mg/mL)
12 μL H$_2$O
4 μL acid phosphatase (0.5 or 2 units)

The reaction solutions were mixed gently and incubated for 90 minutes at 37° C. The reaction solutions were stored at −20° C. for later analysis. For analysis, 7.5 μL acid phosphatase reactions were diluted to 50 μL with 0.1% formic acid in water to a final concentration of 10 μM. The final reactions of 20 μL were analyzed by LCMS with conditions as shown in Table 1 below. The control reactions for enzyme activity were assembled and diluted to 10 mM p-nitrophenylphosphate in place of peptide. After incubation, the reactions were diluted with 0.1 mL of 100 mM borate buffer pH 9 and read at the absorbance of 405 nm to monitor p-nitrophenol appearance.

TABLE 1

| LCMS Analysis | |
| --- | --- |
| MS: | Thermo Scientific LTQ Orbitrap Discovery |
| Ion Mode: | Positive ion electrospray (ESI$^+$) |
| Scan Range: | 200-2000 m/z |
| HPLC: | Waters Acquity UPLC |
| Column: | Thermo Hypersil Gold aQ, 2.1 × 50 mm, 1.9 μm |
| Flow Rate: | 400 μL/min |
| Column Temperature | 40° C. |

TABLE 1-continued

LCMS Analysis

| Autosampler Temperature: | 4° C. | | |
|---|---|---|---|
| Injection Volume: | 20 µL | | |
| Mobile Phases: | A = 0.1% formic acid in H$_2$O | | |
| | B = 0.1% formic acid in 85:15 (v/v) acetonitrile:methanol | | |

| Gradient: | Time (min) | % A | % B |
|---|---|---|---|
| | 0 | 98 | 2 |
| | 2.4 | 98 | 2 |
| | 25.2 | 20 | 80 |
| | 26.2 | 20 | 80 |
| | 27.2 | 10 | 90 |
| | 30.2 | 98 | 2 |
| | 35 | 98 | 2 |

Tables 2 and 3 show that under the conditions used for assay, 0.5 units of calf intestinal alkaline phosphatase (pH 8) and 0.5 units of either potato acid phosphatase or human prostate acid phosphatase (pH 5) efficiently hydrolyzed p-nitrophenylphosphate.

The sensitivity of Peptide 1 and Peptide 2 to phosphatase treatment was assessed by analyzing the reaction products by LC-MS. Tables 2 and 3 show that at pH 8 calf intestinal alkaline phosphatase efficiently dephosphorylated Peptide 1 and Peptide 2. In contrast to alkaline phosphatase, potato acid and human prostate gland acid phosphatases were very inefficient in dephosphorylating Peptide 1 under conditions where they efficiently hydrolyzed p-nitrophenylphosphate (Table 2). Human prostate gland acid phosphatase was also very inefficient in dephosphorylating Peptide 2 (Table 3).

As a separate control, Peptide 3 was treated with and without calf intestinal alkaline phosphatase and the resulting reactions were analyzed by LC-MS. Peptide 3 was not affected by CIP treatment (data not shown)

TABLE 2

Dephosphorylation of Peptide 1

| | p-nitrophenylphosphate | | Peptide 1 | |
|---|---|---|---|---|
| Substrate | Remaining (%) | Dephospho (%) | Remaining (%) | Dephospho (%) |
| Alkaline phosphatase pH 8 | 0 | 100 | 0 | 100 |
| Potato acid phosphatase pH 5 | 0 | 100 | 77.8 | 22.1 |
| Human prostatic acid phosphatase pH 5 | 0 | 100 | 93.8 | 6.2 |

TABLE 3

Dephosphorylation of Peptide 2

| | p-nitrophenylphosphate | | Peptide 2 | |
|---|---|---|---|---|
| Substrate | Remaining (%) | Dephospho (%) | Remaining (%) | Dephospho (%) |
| Alkaline phosphatase pH 8 | 0 | 100 | 0 | 100 |
| Human prostatic acid phosphatase pH 5 | 0 | 100 | 95.9 | 4.1 |

Example 2 cGMP Accumulation in T84 Cells for Analysis of GC-C Activity

For the cGMP assay, 4.5×10$^5$ cells/mL of T84 cells were grown overnight in 24 well tissue culture plates. On the next day, the T84 cells were washed twice with 1 mL of DMEM+ 20 mM MES (pH 5) or DMEM+50 mM sodium bicarbonate (pH8) in which these buffers did not contain serum. After the second wash, the cells were incubated with 450 µL of 1 mM isobutylmethylxanthine (IBMX) in either the pH 5 or pH 8 buffers for 10 minutes at 37° C. to inhibit any phosphodiesterase activity. The peptides were then diluted in either pH 5 or pH 8 buffer to a 10× concentration. The peptide solution of 50 µL was diluted to a final volume of 500 µL with the T84 cells, bringing each peptide concentration to 1×. An eleven point curve analysis was conducted for each peptide, with final peptide concentrations tested in each assay, in nM: 10000, 3000, 1000, 300, 100, 30, 10, 3, 1, 0.3, 0.1.

There was no peptide control used to determine endogenous levels of cGMP. Peptides were incubated for 30 minutes at 37° C. After 30 minutes, the supernatants were removed and the cells were lysed with 0.1 M HCl. The cells were lysed for 30 minutes on ice. After 30 minutes, lysates were pipetted off and placed into a 96 well HPLC plate and spun at 10,000×g for 10 minutes to remove any cell debris. Supernatants from the previous spin were removed and placed into a fresh 96 well HPLC plate. Samples were diluted with an equal volume of 1 M ammonium acetate (pH 7) to neutralize samples for better chromatography. A 2×cGMP standard curve was prepared in 0.1 M HCl and then diluted with an equal volume of 1 M ammonium acetate, with the following final concentrations in nM: 1024, 512, 256, 128, 64, 32, 16, 8, 4, 2, 1.

cGMP concentrations were determined from each sample using the LC/MS conditions in Table 4 and a calculated standard curve. EC$_{50}$ values were calculated from concentration-response curves generated with GraphPad Prism Software.

TABLE 4

LC/MS Conditions:

| MS: | Thermo Quantum | | | | |
|---|---|---|---|---|---|
| Ion Mode: | ESI$^+$ | | | | |
| Scan Type: | MRM | | | | |

| Compound: | Transition | Dwell Time (msec) | Collision Energy (V) | Tube Lens | Retention Time (min) |
|---|---|---|---|---|---|
| cGMP | 346 > 152 | 100 | 28 | 139 | 1.0 |

| HPLC: | Agilent Technologies 1200 Series with CTC Analytics HTS PAL |
|---|---|
| Column: | Thermo Hypersil Gold 2.1 × 50 mm, 5 micron particle size |
| Flow Rate: | 400 µL/min |
| Column Temperature | RT |
| Autosampler Temperature: | 6° C. |
| Injection Volume: | 20 µL |
| Mobile Phases: | A = 98:2 Water:Acetonitrile + 0.1% Formic Acid |
| | B = 2:98 Water:Acetonitrile + 0.1% Formic Acid |

TABLE 4-continued

LC/MS Conditions:

| Gradient: | Time (min) | % A | % B |
|---|---|---|---|
| | 0 | 100 | 0 |
| | 0.3 | 30 | 70 |
| | 2.00 | 30 | 70 |
| | 2.01 | 100 | 0 |
| | 4 | 100 | 0 |

The ability of Peptide 1 and Peptide 2 and their dephosphorylated forms to stimulate cGMP synthesis in human T84 cells at pH 5 was tested by incubating the cells with the peptides followed by determination of the accumulated intracellular cGMP by LC-MS. Table 5 shows that Peptide 1 and Peptide 2 have potencies similar to that of Peptide 3 in stimulating cGMP synthesis at pH 5. However, dephosphorylated Peptide 1 and Peptide 2 were less potent in the T84 assay than Peptide 3.

TABLE 5 cGMP response of T84 cells

| Peptide | $EC_{50}$ at pH 5 (nM) |
|---|---|
| Peptide 3 | 16 |
| Peptide 1 | 9.8 |
| Dephospho-Peptide 1 | 128 |
| Peptide 2 | 10.4 |
| Dephospho-Peptide 2 | 78.1 |

The cGMP response of T84 cells to Peptide 5 and Peptide 6 were also measured in duplicate in a similar fashion to that described above. The $EC_{50}$ at pH 5 for Peptide 5 was 14.7 nM and the $EC_{50}$ at pH 5 for Peptide 6 was 39.2 nM.

Example 3

Competitive Radioligand-Binding on T84 Cells

Intact human T84 cells from the American Type Culture Collection (ATCC; Manassas, Va.) were used for competitive radioligand-binding experiments. The T84 cells were grown in monolayers on T-150 plastic flasks to 60-70% confluency in Dulbecco's Modified Eagle Medium: Ham's F-12 50/50 media (DMEM/F12)+5% fetal bovine serum (FBS). The cells were harvested by gentle scraping with a cell scraper and cells collected by centrifuge at 2000 g for 10 minutes at 4° C. The cells were washed twice by resuspending gently in phosphate buffered saline (PBS) and collecting them by centrifugation as above.

[$^{125}$I]-STp radioligand was prepared by dissolving one hundred micrograms (100 μg) of NTFYCCELCCNPACA-GCY (Enterotoxin STp; Bachem H-6248) in 0.5 mL water and sent to Perkin-Elmer Life and Analytical Sciences (N. Billerica, Mass.) for iodination using the lactoperoxidase method recited in (Marchanolis, J. J., "An enzymic method for the trace iodination of immunoglobulins and other proteins," *Biochem. J.* 1969, 113, 299-305). Perkin-Elmer purified the labeled tracer by HPLC using a Waters C-18 μBondapak column (25 cm) previously equilibrated with 10 mM ammonium acetate pH 5.8. A gradient from 0 to 25% acetonitrile was applied to the column in 60 min, followed by isocratic elution at 25% acetonitrile for another 20 min. This method separated two monoiodinated forms from each other and from unlabeled precursor. The second monoiodinated peak (Peak 2) which eluted after 64 min and corresponded to iodination of the fourth tyrosine, was used as the labeled tracer in the assay. The labeled tracer had a specific activity of 2200 Ci/mmol. Upon arrival, tracer was stored in aliquots at −20° C.

The binding reactions were assembled in duplicate in 0.2 mL containing: 2.5×10$^5$ T84 cells (0.25 mg protein), 200,000 cpm [$^{125}$I]-STp (41 fmol, 200 pM), 0.1 to 3,000 nM competitor, and 0.5% bovine serum albumin (BSA). The binding assays were conducted at pH 5.0 in DMEM/20 mM 2-(N-morpholino) ethanesulfonic acid (MES). The binding assays at pH 8.0 were performed in DMEM/20 mM N-2-Hydroxyethylpiperazine-N'-2-Ethane Sulfonic Acid (HEPES)/50 mM sodium bicarbonate. The control reactions did not contain a competitor (total) or no cells.

The buffer solutions were prepared first, then protease-free BSA was added to 0.5%. The radioligand was added to a final concentration of 0.001 μCi/μL. Preparation of competitor peptide stock solutions were made by dissolving peptides to 1 mg/mL in 50 mM sodium phosphate pH 6.0. Concentrations were calculated from the peptide molecular weight provided in the Certificate of Analysis. Competitor dilutions were made in 50 mM sodium phosphate pH 6.0 that contained 20 times the final concentration of peptide to be tested in the binding reaction (20× competitor).

The binding reactions were assembled in the following order:
i. Radioligand and BSA in buffer solution.
ii. 10 μL of 20× competitor.
iii. T84 cells.

The binding reactions were mixed gently and incubated at 37° C. for 1 h. Separation of membrane-bound from free radioligand was conducted by applying the binding reactions to 2.5 cm Whatman GF/C glass-fiber filters (pretreated with 1% polyvinylpyrrolidone in PBS) using vacuum filtration. The filters were rinsed twice with 5 mL ice-cold PBS buffer and measurements of the trapped radioactivity was conducted in a scintillation counter. The determination of specific binding was made by subtracting the bound radioactivity from a reaction that contained excess competitor (1 μM) from the bound radioactivity of each sample. The generation of competitive radioligand-binding curves were made using GraphPad Prism (GraphPad Software, San Diego, Calif.) and the data was analyzed with nonlinear regression to calculate the concentration of competitor that resulted in 50% radioligand bound ($IC_{50}$). The apparent dissociation equilibrium constant ($K_i$) for each competitor was obtained, from the $IC_{50}$ values and a previously determined estimate of the dissociation constant for the radioligand, $K_d$≅15 nM, using the method of (Cheng and Prusoff, (1973) Biochem. Pharmacol. 22(23) 3099-3108). The radioligand concentration of 200 pM used in the assays was very small compared to its dissociation constant, the calculated $IC_{50}$ and the $K_i$ values (Table 5) were in effect identical.

TABLE 6

Competitive radioligand binding assay

| Peptide | $K_i$ at pH 5 (nM) |
|---|---|
| Peptide 3 | 1.2 |
| Peptide 1 | 1.1 |
| Dephospho-Peptide 1 | 10.5 |
| Peptide 2 | 0.6 |
| Dephospho-Peptide 2 | 4.5 |

Table 6 shows that Peptide 1 and Peptide 2 have potencies similar to that of Peptide 3 in binding at pH 5. However, dephosphorylated Peptide 1 and Peptide 2 have lower affinities for GC-C than Peptide 3 in the binding assay.

Example 4

Gastrointestinal Transit in Mice

The purpose of the assay was to test the effect of the guanylate cyclase C agonist peptides on in vivo gastrointestinal transit in mice. Orally-dosed guanylate cyclase C agonists have been demonstrated to increase the % distance travelled by a charcoal meal in mice.

For the assay, female CD-1 mice (n=10 per group) weighing 25-30 g were fasted overnight and given access to water ad libitum. Activated charcoal (20 g; 100 mesh; Sigma cat#242276) was suspended in 200 mL gum arabic (100 mg/mL), and stirred for at least one hour. Test peptides were prepared in a 20 mM Tris pH 6.9 vehicle.

Test peptide and vehicle were administered in 200 µL doses by oral gavage. Seven minutes after dosing the test peptides, 200 µL of the charcoal/gum arabic suspension was dosed by oral gavage. After 15 minutes, mice were sacrificed by $CO_2$ overdose. The gastrointestinal tract was removed from the esophagus to the caecum. The total length of the small intestine was measured from the pyloric junction to the ileocaecal junction. The distance travelled by the charcoal was measured from the pyloric junction to the charcoal front. The distance travelled (%) was determined as (distance travelled by charcoal/total length of the small intestine)×100. Data were entered into the GraphPad Prism software program and analyzed by ANOVA using a Bonferroni multiple comparison test post-hoc. Plots of data and $ED_{50}$ were also determined using the GraphPad Prism software package.

The dose-dependent effects of acute doses of Peptide 4, Peptide 1, Peptide 2, the dephosphorylated form of Peptide 1 and the dephosphorylated form of Peptide 2 on GI transit were determined in female CD mice. The distance traveled by the charcoal front after seven minutes, expressed as a percent of total length of small intestine was used to calculate $ED_{50}$ values (Table 7).

TABLE 7

Acceleration of upper GI transit in mice

| Peptide | $ED_{50}$ (µg/kg) |
| --- | --- |
| Peptide 4 | 2.06 |
| Peptide 1 | 5.61 |
| Dephospho-Peptide 1 | 12.7 |
| Peptide 2 | 2.47 |
| Dephospho-Peptide 2 | 6.03 |

Table 7 shows that the dephosphorylated forms of Peptide 1 and Peptide 2 exhibited reduced potency when compared to their respective peptides when administered orally in the upper GI transit model in mice.

Example 5

Fluid Secretion in Rat Intestinal Loops

The effect of GC-C agonist peptides on secretion was studied by injecting GC-C agonist peptides described herein directly into an isolated loop in wild-type rats.

Loops were isolated by surgically ligating three loops in the small intestine of the rat. The methodology for ligated loop formation was similar to that described in (London et al., 1997, Am J Physiol, p. G93-105). The loops were roughly centered and at lengths of 1-3 cm. The loops were injected with 200 µl of either peptide/GC-C agonist (0.1-5 µg) or vehicle (20 mM Tris, pH 7.5 or Krebs Ringer, 10 mM Glucose, HEPES buffer (KRGH)). Following a recovery time of up to 90 minutes the loops were excised. Weights were recorded for each loop before and after removal of the fluid contained therein. The length of each loop was also recorded. A weight to length ratio (W/L) for each loop was calculated to determine the effects of the GC-C agonist peptide described herein on secretion. Loop fluid volume was also determined.

Data showing increases in fluid secretion, pH increase and bicarbonate secretion in ligated duodenal loops in rats are shown in FIG. 2 and Table 8. FIG. 2 shows that Peptide 2 has a potency similar to that of Peptide 4 with regard to induction of fluid accumulation in ligated rat duodenal loops. Table 8 provides the results in ligated rat duodenal loops using 2.5 µg of peptide per loop.

TABLE 8

Fluid secretion, pH increase, and bicarbonate secretion

| Peptide | Rate of fluid accumulation µL/min/cm | pH | Rate of $HCO_3^-$ accumulation Meq/min/cm |
| --- | --- | --- | --- |
| Vehicle | 0.5 | 7.5 | 0.00002 |
| Peptide 4 | 2.0 | 8.2 | 0.00008 |
| Peptide 2 | 2.3 | 8.1 | 0.00008 |
| Dephospho-Peptide 2 | 2.3 | ND | ND |
| Peptide 1 | 1.8 | 7.7 | 0.00007 |
| Dephospho-Peptide 1 | 2.0 | 7.7 | 0.00008 |

Example 6

In Vitro Metabolism in Mouse Jejunum Loop Fluid

The purpose of this study was to determine the stability of phosphorylated peptides in mouse jejunal loop fluid. Peptide 2, dephosphorylated-peptide 2 (dephospho-peptide 2), peptide 3, and isotopically labeled peptide 2 were used in the study. The isotopically labeled peptide 2 was synthesized with $^{13}C$, $^{15}N$-labeled alanine and leucine (i.e., with a sequence CCpS[$^{13}C_6$, $^{15}N$]LCCNP[$^{13}C_6$, $^{15}N$]ACTGC).

Each peptide was synthesized by American Peptide Company, Inc., and was stored desiccated at −20° C. A 1 mg/mL solution for each of the non-labeled peptides was prepared in 1 M tris(hydroxymethyl)aminomethane hydrochloride (Tris-HCl), pH 8 just prior to conducting the mouse intestinal loop fluid assay. A 500 ng/mL solution of $^{13}C$, $^{15}N$-labeled peptide 2 was prepared in 0.1% formic acid in water and was utilized to dilute the jejunum samples for post-assay LC-MS/MS analysis.

To study the metabolism of peptide 2, dephospho-peptide 2, and peptide 3 in vitro, the peptides were incubated in mouse jejunum fluid extracted from loops ligated in the small intestine of mice. To collect the fluid, mice were fasted overnight with full access to water. They were then anesthetized with isofluorane for surgery and subjected to laparotomy in which the small intestine was exteriorized. Jejunum loops of 3 to 4 cm in length were made with sutures starting at 7 cm from the pyloric sphincter of the stomach. Once the loops were formed, they were injected with 200 µL of phosphate buffered saline (PBS) buffer (10 mM, pH 7.4). The abdominal wall and skin of the animals were then sutured, and the animals were allowed to recover for 30 minutes. Following recovery, the animals were sacrificed, the loops were then excised and the fluid inside was recovered and stored at −80° C. until use.

For each peptide, 25 µL of the 1 mg/mL peptide stock solution was added to 25 µL of 1 M Tris-HCl and 25 µL of 10× calf intestinal phosphatase (CIP) buffer containing 500 mM Tris-HCl, 1 M sodium chloride (NaCl), 0.1 mM magnesium chloride ($MgCl_2$), pH 8. The reactions were initiated by adding 175 µL of the mouse jejunum loop fluid or 175 µL of the 1 M Tris-HCl pH8 buffer for the control reactions. The final concentration of each peptide was 100 µg/mL. The reactions were continuously mixed and maintained at 37° C. on a plate shaker. At 0, 2, 5, 10, 20, 30, 60, 90 and 120 minutes after adding the mouse intestinal loop fluid, a 25 µL aliquot was taken and added to 25 µL of 4° C. 12% trichloroacetic acid to stop the reaction. An additional 200 µL of 0.1% formic acid in water was added to these reactions for dilution purposes. These samples were then further diluted by taking 20 µL of each sample and adding it to 480 µL of 0.1% formic acid in water containing 500 ng/mL of the internal standard 13C, 15N-labeled peptide 2.

The concentration of peptide 2, dephospho-peptide 2, and peptide 3 in the samples were measured by LC-MS/MS. All samples were analyzed using an Applied Biosystems/MDS SCIEX API 4000 triple quadrupole mass spectrometer equipped with a high-performance liquid chromatography (HPLC) system. The mass spectrometer was operated in multiple reaction monitoring (MRM) mode, with resolution set to 1.2 Da. The instrument and chromatographic parameters for each compound are summarized in Table 9.

TABLE 9

Peptide 2, dephospho-peptide 2 (dephosp.-Pep. 2), peptide 3, and $^{13}C$, $^{15}N$ - labeled peptide 2 (iso-lab.-Pep. 2) LC-MS/MS Method Parameters

| MS: | Applied Biosystems API 4000 |
| --- | --- |
| Ion Mode: | ESI+ |
| Scan Type: | MRM |

| Compound: | Transition | Dwell Time (msec) | Dwell Potential (V) | Collision Energy (V) | Cell Exit Potential (V) | Retention Time (min) |
| --- | --- | --- | --- | --- | --- | --- |
| Peptide 2 | 677 > 627 | 100 | 65 | 20 | 11 | 2.5 |
| Dephosp.-Pep.2 | 636 > 627 | 100 | 65 | 20 | 11 | 2.5 |
| Peptide 3 | 740 > 182 | 100 | 65 | 30 | 14 | 2.5 |
| Iso-lab.-Pep.2 | 682 > 633 | 100 | 65 | 20 | 11 | 2.5 |

| HPLC: | Agilent Technologies 1200 Series |
| --- | --- |
| Column: | Atlantis T3, 2.1 × 50 mm, 5 µM (PN: 186003737) |
| Flow Rate: | 400 µL/min |
| Column Temperature | 40° C. |
| Autosampler: | 6° C. |
| Injection Volume: | 20 µL |
| Mobile Phases: | A = 0.1% formic acid in water<br>B = 0.1% formic acid in 85:10:5 (v:v:v) acetonitrile:isopropyl alcohol:$H_2O$ |

TABLE 9-continued

Peptide 2, dephospho-peptide 2 (dephosp.-Pep. 2), peptide 3, and $^{13}C$, $^{15}N$ - labeled peptide 2 (iso-lab.-Pep. 2) LC-MS/MS Method Parameters

| Gradient: | Time (min) | % A | % B |
| --- | --- | --- | --- |
| | 0 | 98 | 2 |
| | 0.5 | 98 | 2 |
| | 0.6 | 20 | 80 |
| | 2.0 | 20 | 80 |
| | 2.1 | 98 | 2 |
| | 5.0 | 98 | 2 |

The LC-MS/MS data were processed using Analyst version 1.4.2 software (Applied Biosystems/MDS SCIEX). The peak area ratio (ratio of analyte peak area to internal standard peak area) was used to calculate the percent remaining of each peptide.

Figure 3:
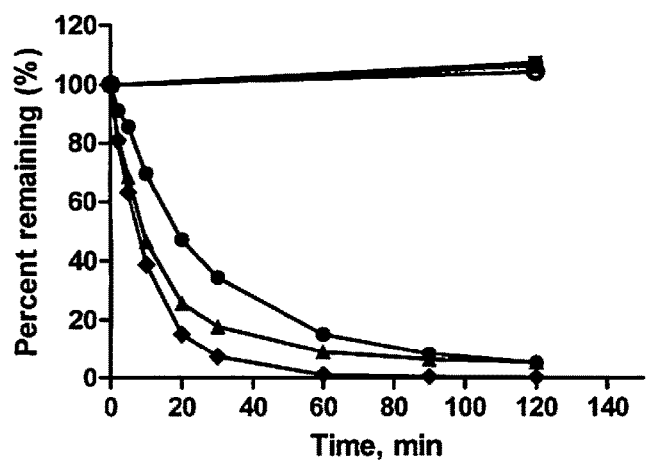
FIG. 3 presents the results of a study on the stability of Peptide 2, Dephospho-peptide 2, and Peptide 3 in mouse intestinal (jejunum) fluid.

FIG. 3 displays the percent remaining of peptide 2 and dephospho-peptide 2, and peptide 3 at the nine time points measured during the 120 minute incubation in mouse jejunum fluid and in the control reaction (1 M Tris-HCl) at 37° C. After the incubation in the mouse jejunal loop fluid, only 5.3% of peptide 2 remained after 120 minutes. The metabolite, dephospho-peptide 2, was formed in this reaction and increased in concentration for the first 20 minutes then showed a slow decrease for the remaining time. In the control reaction, peptide 2 was not metabolized and no dephospho-peptide 2 was formed. After the incubation in the mouse jejunum fluid, only 5.6% of the dephospho-peptide 2 remained after 120 minutes. In contrast, dephospho-peptide 2 was not metabolized in the control reaction. Peptide 3 was rapidly metabolized and was not detected after 90 minutes in the mouse jejunum fluid. In the control reaction, peptide 3 was not metabolized.

Peptide 2, its metabolite dephospho-peptide 2, and peptide 3 were metabolized in mouse jejunum loop fluid. Formation of dephospho-peptide 2 was observed when peptide 2 was incubated in mouse jejunum loop fluid at 37° C. Dephospho-peptide 2 and peptide 3 were degraded faster in mouse intestinal fluid than peptide 2.

Example 7

Evaluation of the Anti-Nociceptive Effects of 0.03, 0.3, 10 µg/Kg Doses of Peptide 2 on Basal and Post-Inflammatory Colorectal Hypersensitivity to Distension in Male Wistar Rats The objective of this study was to evaluate the effects of low doses (0.03, 0.3, 10 µg/kg) of peptide 2 on basal and post-inflammatory 2,4,6-trinitrobenzene sulfonic acid (TNBS)-induced colorectal hypersensitivity to distension in male Wistar rats.

Materials and Methods

Peptide 2 was prepared at the appropriate concentrations in a 20 mM Tris HCl, pH 6.85 vehicle.

Animals and Surgical Procedures

Groups of male Wistar rats (n=8-10) (Janvier S A, Le Genest St Isle, France) weighing 220-250 grams were used in this study. The rats were housed individually in propylene cages and were surgically prepared for electromyography (EMG) according to a protocol described in (Morteau O et al., Science (1994) 39: 1239-1248). Under general anesthesia induced by intraperitoneal (ip) administration of 0.6 mg/kg acepromazine (Calmivet; Vetoquinol, Lure, France)

and 120 mg/kg ketamine (Imalgene 1000; Rhone Merieux animals), three pairs of nickel-chromium (NiCr) electrodes were each implanted in the striated muscles of the abdomen. The electrodes were exteriorized on the back of the neck and protected by a glass tube attached to the skin.

EMG recordings were initiated five days after surgery. The electrical activity was recorded with an electromyograph (Mini VIII, Alvar, Paris, France) using a short time constant (0.03 seconds) to remove low-frequency signals (<3 Hz) and a paper speed of 3.6 cm/minute.

During the experiment, the number of spike bursts on the EMG recordings that corresponded to abdominal contractions was determined per 5 minute periods.

TNBS Administration

Rats were fasted overnight. Following the fasting period, 2,4,6-trinitrobenzene sulfonic acid (TNBS; 80 mg/kg in 0.3 ml 50% ethanol) was infused intrarectally (ir) through a silicone catheter that was surgically introduced under anesthesia at 4 cm from the anus using the method of Morteau et al. to induce colonic inflammation.

Colorectal Distension Procedure and Colorectal Volume Recordings

Rats were accustomed to polypropylene tunnel devices (diameter: 7 cm; length: 20 cm) during three days (3 h/day) prior to the start of colorectal distension (CRD) procedures to minimize recording artifacts caused by movement of the animals. The balloon used for distension was 4 cm in length and was prepared from a latex condom fixed on a rigid catheter taken from an embolectomy probe (Fogarty). The balloon was inserted into the rectum at 1 cm from the anus and fixed at the basis of the tail. Isobaric distensions were performed from 0 mmHg to 60 mmHg by connecting the balloon to a computerized barostat. The first distension was performed at a pressure of 15 mmHg, and an increment of 15 mmHg was added at each following step until a maximal pressure of 60 mmHg, with each distension step lasting for a period of 5 min. Colonic pressure and balloon volume were continuously monitored on a potentiometric recorder (L6514, Linseis, Selb, Germany) with a paper speed of 1 cm/minute.

Experimental Design

Figure 4:
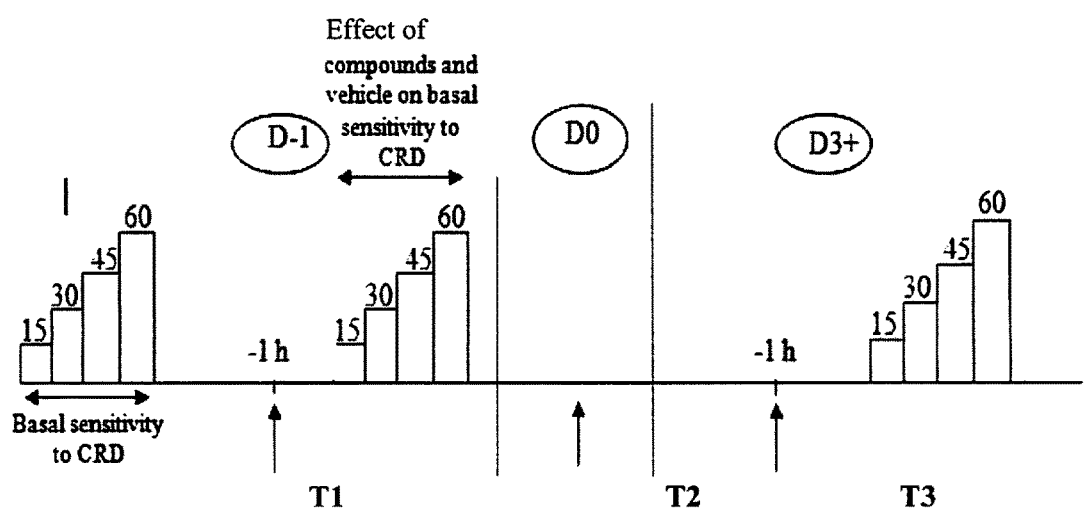
FIG. 4 presents a diagram of the experimental schedule used in Examples 7 and 8.

FIG. 4 presents a diagram of the experimental schedule. Four to six groups of male Wistar rats (n=8-10) were used. A basal sensitivity to colorectal distension was established in each group, with distension pressures increasing by 15 mmHg increments as detailed above. Next, each group was individually orally dosed with either peptide 2 (0.03, 0.3, 10 µg/kg) or vehicle (20 mM Tris HCl, pH 6.85) one hour prior to colorectal distension. CRD treatments were performed as for the basal measurements. The following day, TNBS (80 mg/kg, ir) was administered as described above. Three days after TNBS administration, rats were treated with either peptide 2 (0.03, 0.3, 10 µg/kg) or vehicle (20 mM Tris HCl, pH 6.85) one hour prior to colorectal distension as before. CRD treatments were performed as for the basal measurements.

Statistical analyses on the number of spike bursts that corresponded to abdominal contractions was determined per 5 minute periods was performed by one-way-analysis of variance (ANOVA), followed by Student's unpaired t test when the ANOVA test was significant. In the case of data having non-Gaussian distributions, a Mann-Whitney (non-parametric) test was performed. The data are expressed as the mean±SEM (standard error of the mean). Differences were considered significant for p<0.05.

Results

Figure 5:
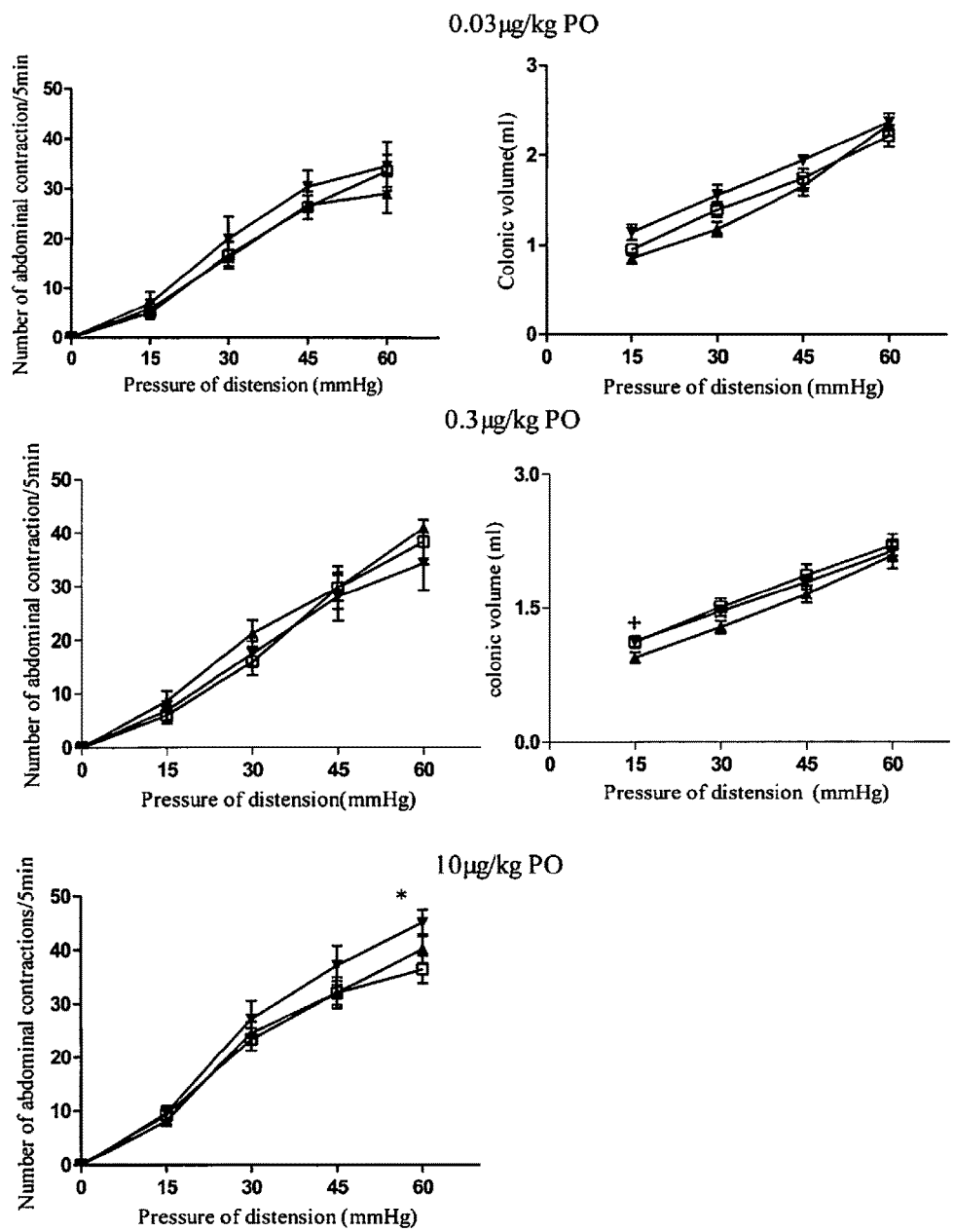
FIG. 5 presents the effect of (0.03, 0.3, 10 μg/kg) of Peptide 2 on the abdominal response to colorectal distension in rats under basal conditions.

As seen in FIG. 5, under basal conditions, colorectal distension was associated with an increase in abdominal contractions and changes in colorectal volumes that were proportional to the level of distension pressure applied (15, 30, 45, 60 mmHg). Peptide 2, when administered at 0.03 µg/kg, 0.3 µg/kg or 10 µg/kg, had no effect on the number of abdominal contractions and colonic volumes, compared to vehicle (colonic volume measurements at 10 µg/kg were not performed in this study, but note that this dose had no effect in Example 8).

As seen in FIG. 6, three days after intrarectal installation of TNBS (colorectal inflammatory allodynia), the number of abdominal contractions was significantly increased at 15 mmHg distension pressure (p<0.05). Peptide 2, orally administered at 0.03 µg/kg, had no significant effect on TNBS-induced colorectal hypersensitivity at all distension pressures tested (15, 30, 45, 60 mmHg), compared to vehicle. Orally administered peptide 2 at 0.3 µg/kg significantly decreased colorectal hypersensitivity at all distension pressures tested (15 mmHg: p<0.001; 30 mmHg: p<0.01; 45 mmHg: p<0.05; 60 mmHg: p<0.01), while an oral dose of 10 µg/kg significantly decreased colorectal hypersensitivity at 15 mmHg distension pressure (p<0.01), compared to vehicle. Peptide 2, orally administered at 0.03 µg/kg, significantly decreased colonic volumes at all distension pressures tested (15 mmHg: p<0.01; 30, 45, 60 mmHg: p<0.001), but had no effect when orally administered at 0.3 µg/kg and 10 µg/kg, compared to vehicle.

Under basal conditions, orally administered peptide 2 (0.03, 0.3, 10 µg/kg) had no effect on colorectal hypersensitivity and colonic volumes, compared to vehicle. In post-inflammatory conditions, orally administered peptide 2 (0.3 µg/kg, 10 µg/kg) significantly decreased colorectal hypersensitivity, compared to vehicle. After an oral dose of 0.03 µg/kg of peptide 2, colonic volumes are significantly decreased, but were not affected after oral doses of 0.3 µg/kg and 10 µg/kg, respectively, compared to vehicle.

Example 8

Evaluation of the Anti-Nociceptive Effects of Higher Doses (3, 10, 30 µg/kg) of Peptide 2 on Basal and Post-Inflammatory Colorectal Hypersensitivity to Distension in Male Wistar Rats The objective of this study was to evaluate the effects of higher doses (3, 10, 30 µg/kg) on basal and post-inflammatory (2,4,6-trinitrobenzene sulfonic acid (TNBS)-induced) colorectal hypersensitivity to distension in male Wistar rats.

Materials and Methods

Materials and methods were as described above in Example 7. All animal husbandry and surgical treatments, TNBS administration followed the protocols described in Example 7.

Groups of male Wistar rats (n=8-10) were used. The experimental schedule was the same as described in Example 7 and FIG. 4, except that animals were orally dosed with higher doses (3, 10, 30 µg/kg) of peptide 2.

Data was analyzed as in Example 7.

Results

Figure 7:
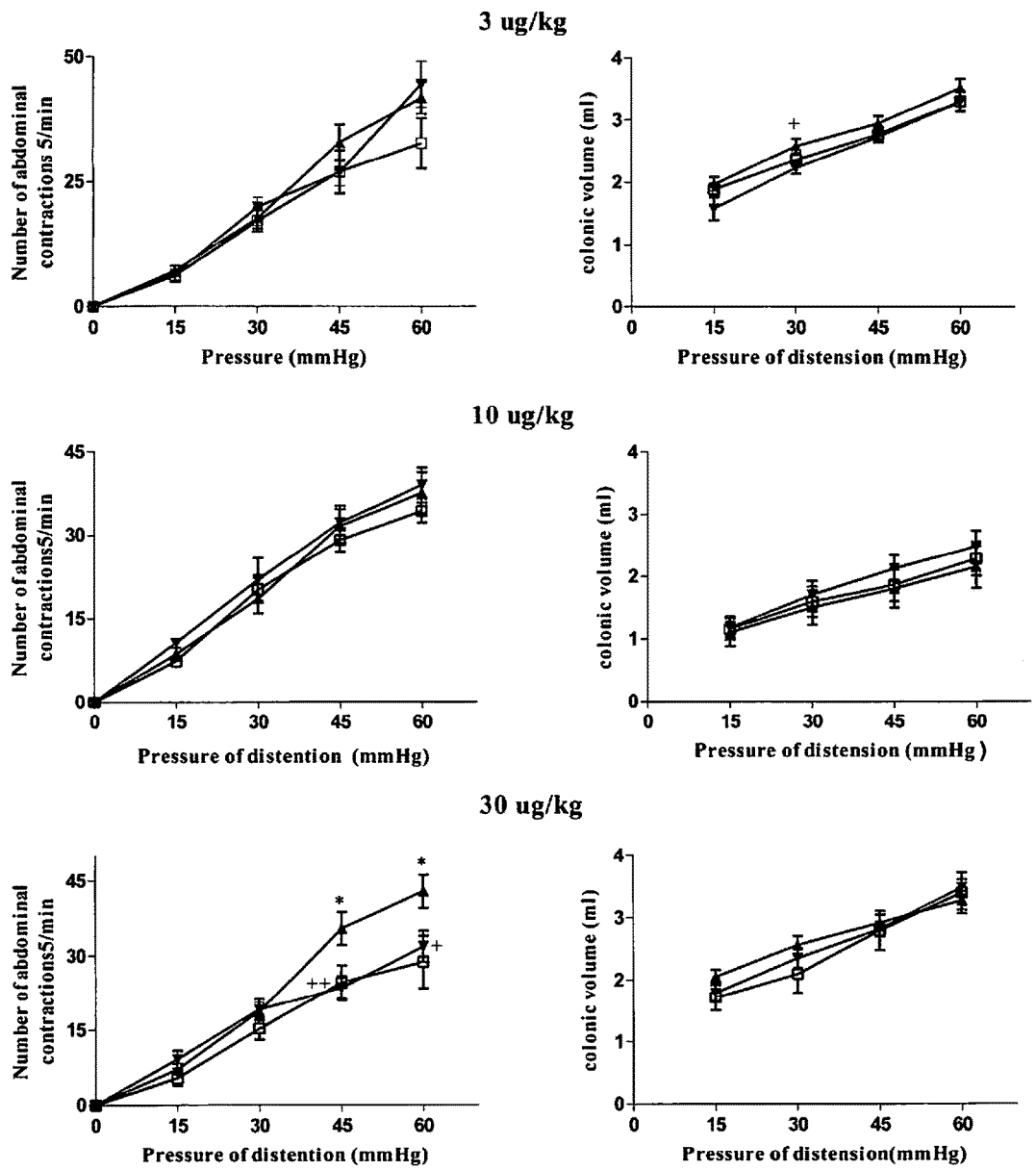
FIG. 7 presents the effect of (3, 10, 30 μg/kg) of Peptide 2 on the abdominal response to colorectal distension in rats under basal conditions.

As seen in FIG. 7, under basal conditions, colorectal distension was associated with an increase in abdominal contractions and changes in colorectal volumes that were proportional to the level of distension pressure applied (15, 30, 45, 60 mmHg). Peptide 2, when orally administered at doses of 3 µg/kg and 10 µg/kg, had no effect on the number of abdominal contractions and the colonic volumes at all distension pressures tested (except p<0.05 at 30 mmHg on colorectal volume at 3 µg/kg), compared to vehicle. Peptide 2, orally administered at 30 µg/kg, significantly decreased the number of abdominal contractions at 45 mmHg (p<0.01) and 60 mmHg distension pressures (p<0.05), compared to vehicle, but had no effect on colorectal volumes.

As seen in FIG. 8, three days after intrarectal installation of TNBS (colorectal inflammatory allodynia), the number of abdominal contractions was significantly increased at 15 mmHg distension pressure (p<0.01). Orally administered peptide 2 (3, 10, 30 µg/kg) significantly decreased the number of abdominal contractions at 15 mmHg distension pressure (p<0.001, p<0.01, p<0.001, respectively), compared to vehicle. Oral doses of 3 µg/kg and 30 µg/kg significantly decreased the number of abdominal contractions at 30 mmHg distension pressure (p<0.001 and p<0.001, respectively), and oral doses of 104 kg and 30 µg/kg significantly decreased the number of abdominal contractions at 60 mmHg distension pressure (p<0.01 and p<0.01, respectively), compared to vehicle. Peptide 2 had no effect on colorectal volumes at all doses tested.

Under basal conditions, orally administered peptide 2 significantly decreases colorectal hypersensitivity at the highest dose (30 µg/kg). Three days after TNBS instillation, orally administered peptide 2 at all doses tested (3, 10, 30 µg/kg) significantly decreases TNBS-induced colorectal hypersensitivity, but has no effect on colonic volumes.

Example 9

The Effects of Peptide 2 on Basal and Stress-Induced Colorectal Hypersensitivity to Distension in Female Wistar Rats The objective of this study was to evaluate the effects of peptide 2 on basal and stress-induced colorectal hypersensitivity to distension in female Wistar rats.

Materials and Methods

Peptide 2 was prepared at the appropriate concentrations in a 20 mM Tris HCl, pH 6.85 vehicle.

Female Wistar rats (Janvier S A, Le Genest St Isle, France) weighing 220-250 grams were used in this study. Husbandry of the animals and EMG implantation and recording were performed as described in Example 7.

The colorectal distension procedure and intestinal volume recordings were performed as described in Example 7.

Partial Restraint Stress

Partial restraint stress (PRS), a relatively mild form of stress, was performed as previously described in (Williams et al. American Journal of Physiology (1987) 253: G582-G586). Briefly, rats were lightly anaesthetized with ethyl-ether, and their freeholders, upper forelimbs and thoracic trunk were wrapped in a confining harness of paper tape to restrict, but not to prevent body movement, and placed in their home cages for two hours. PRS was always performed between 10:00 am and 12:00 pm.

Experimental Design

Figure 9:
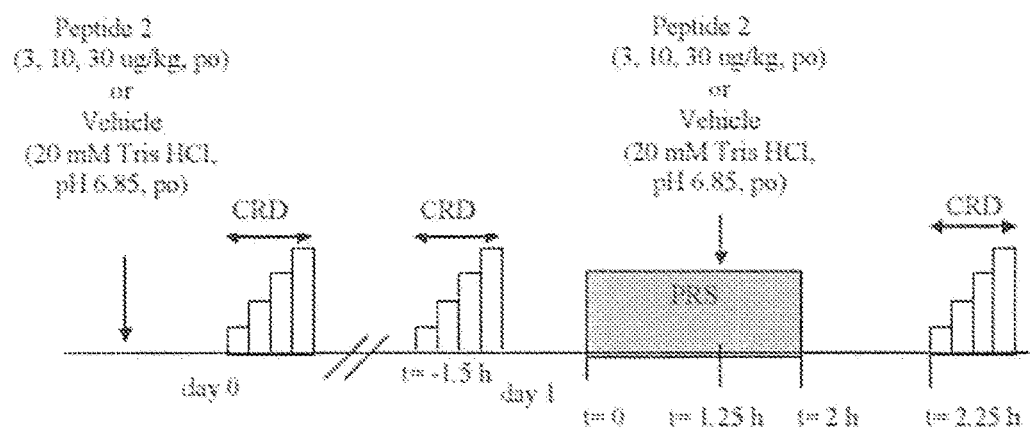
FIG. 9 presents the experimental design of Example 10, measuring the effects of Peptide 2 on basal and stress-induced colonic hypersensitivity to barostatic colorectal distension in rats.

The experimental design of the study is shown in FIG. 9. Groups of female Wistar rats (n=10) were orally dosed with either peptide 2 (3, 10, 30 µg/kg) or vehicle (20 mM Tris HCl, pH 6.85), one hour prior to CRD on day 0. The following day, CRD was performed prior to PRS. Next, 1.5 hours after CRD, the animals were subjected to 2 hours of PRS. Animals were orally dosed with either peptide 2 (3, 10, 30 µg/kg) or vehicle 1.25 hours into the 2-hour stress session. Fifteen minutes after PRS, the animals were subjected to CRD.

Comparisons of the number of abdominal contractions for each 5-minute period during rectal distension were performed using the non-parametric Wilcoxon test for paired data (same group before and after stress session) or the non-parametric Mann-Whitney test for unpaired data (comparison of vehicle group versus peptide 2 group). The data are expressed as the mean±SEM. Differences were considered significant for p<0.05.

Results

Figure 10:
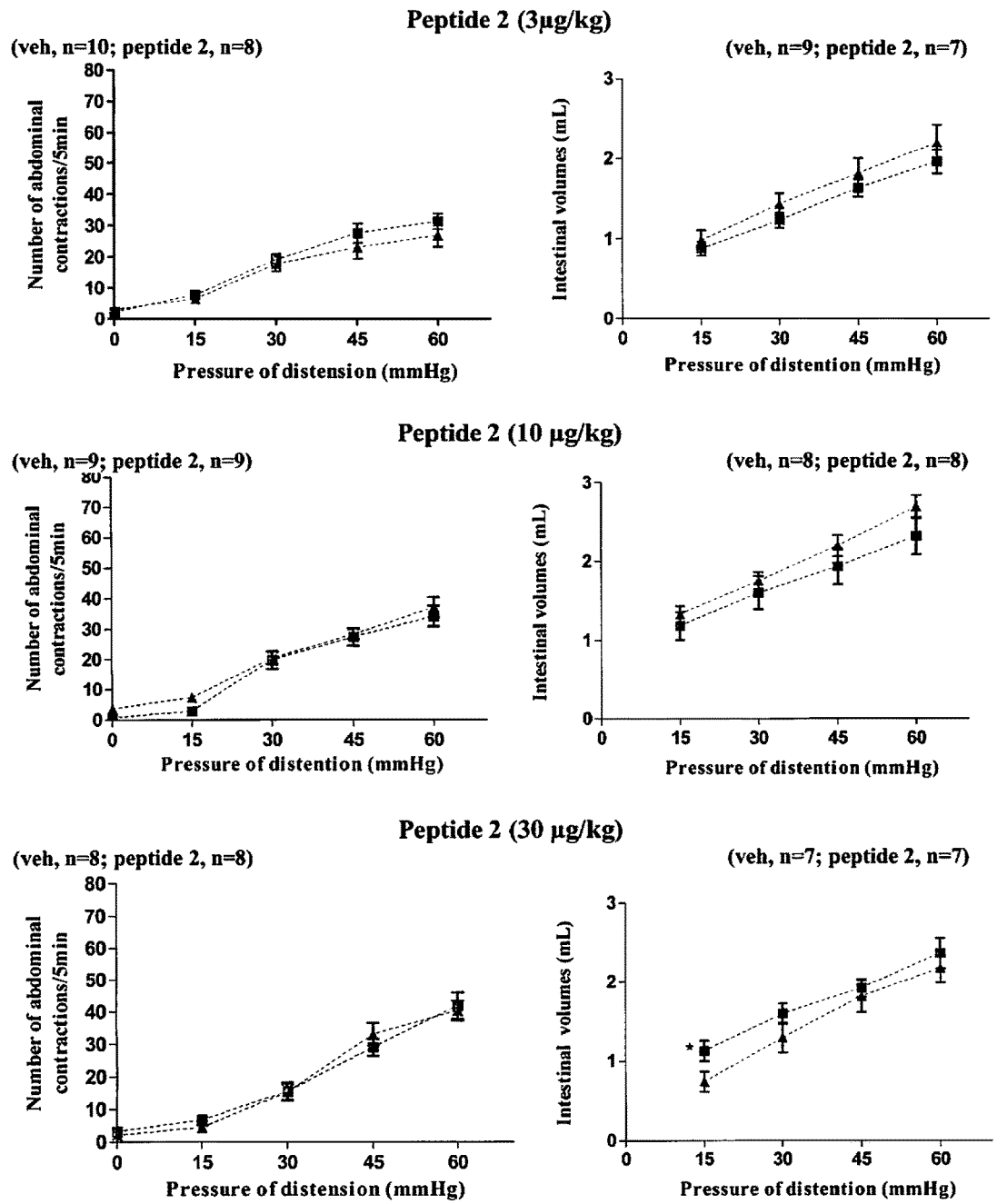
FIG. 10 presents the effect of Peptide 2 on the abdominal response to colorectal distension in female Wistar rats under basal conditions.

FIG. 10 shows that under basal conditions, at all distension pressures tested, orally dosed peptide 2 (3, 10, 30 µg/kg) had no effect on colorectal sensitivity to distension or colonic volumes, compared to vehicle.

Figure 11:
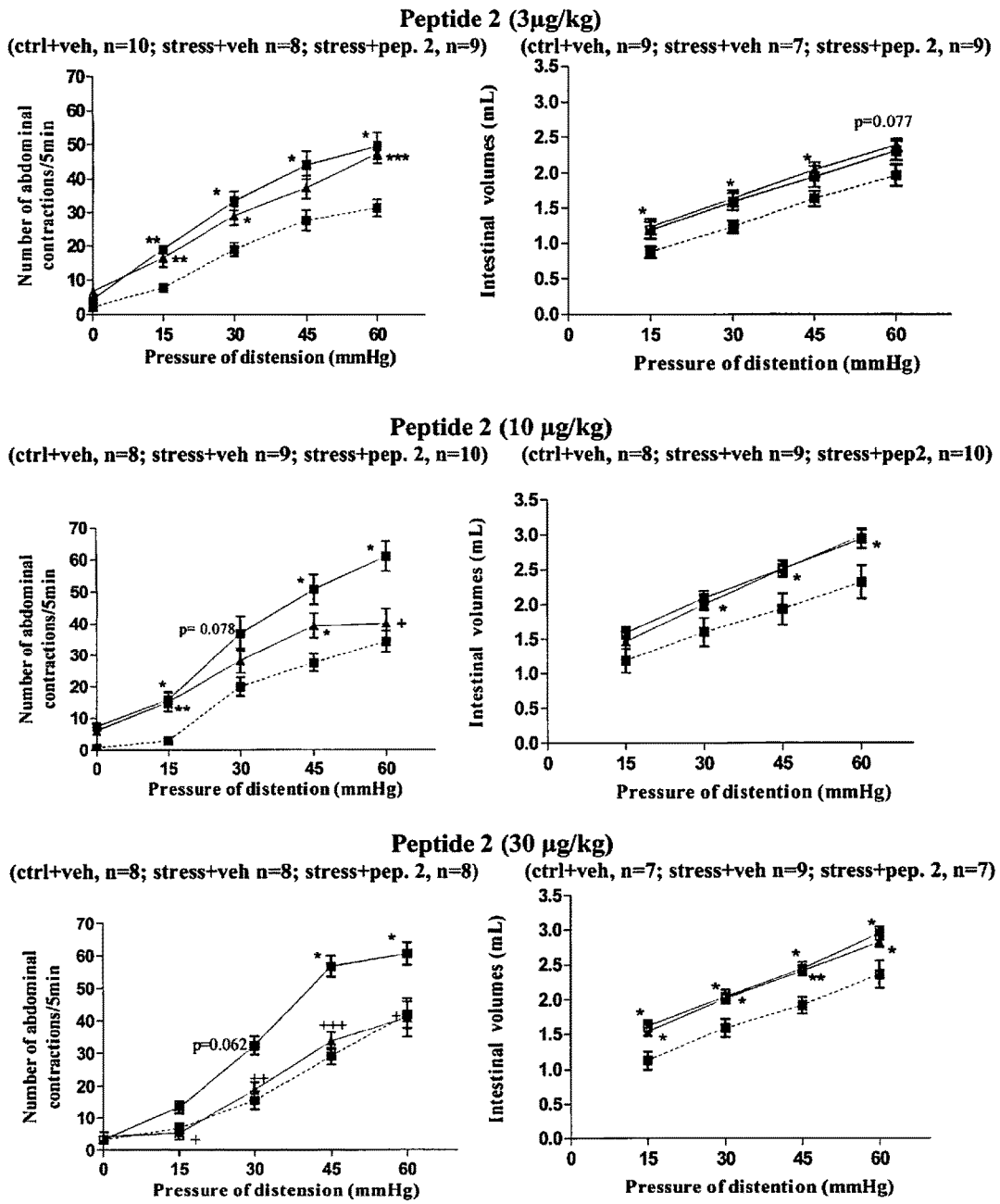
FIG. 11 presents the effect of Peptide 2 on the abdominal response to colorectal distension in female Wistar rats after stress-induced colorectal hypersensitivity.

FIG. 11 shows that following a 2-hour partial restraint stress session, female Wistar rats exhibited a significantly increased abdominal response to colorectal distension at all distension pressures tested (15, 30, 45, 60 mmHg), compared to vehicle. Orally dosed peptide 2 (3 µg/kg) had no effect on the stress-induced abdominal response, compared to vehicle. Peptide 2, orally administered at 10 µg/kg, significantly decreased the number of abdominal contractions at 60 mmHg distension pressure (p<0.05), compared to vehicle. When orally administered at 30 µg/kg, peptide 2 significantly decreased the number of abdominal contractions at all distension pressures tested (15 mmHg: p<0.05); 30 mmHg: p<0.01; 45 mmHg: p<0.001; 60 mmHg: p<0.05), compared to vehicle. Following a 2-hour partial restraint stress session, the stress-induced colorectal volumes were significantly increased at all distending pressures, compared to vehicle under basal conditions. Orally administered peptide 2 (3, 10, 30 µg/kg) had no effect on the stress-induced increase in colorectal volumes, compared to vehicle.

OTHER EMBODIMENTS

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A method for treating a lower gastrointestinal (GI) disorder in a patient in need thereof:

and/or a method for treating, preventing or reducing visceral or abdominal pain or discomfort associated with a lower GI disorder in a patient in need thereof, comprising administering a pharmaceutical composition comprising a peptide or a pharmaceutically acceptable salt thereof, wherein the peptide comprises the amino acid sequence $Xaa_1$ $Xaa_2$ $Xaa_3$ $Xaa_4$ $Cys_5$ $Xaa_6$ $Xaa_7$ $Xaa_8$ $Cys_9$ $Asn_{10}$ $Pro_{11}$ $Ala_{12}$ $Cys_{13}$ $Xaa_{14}$ $Gly_{15}$ $Xaa_{16}$ $Xaa_{17}$ (SEQ ID NO:1), or a pharmaceutically acceptable salt thereof; wherein $Xaa_1$ is Asn, D-Asn, Gln, D-Gln, Pro, Ala, β-Ala, D-Ala, Val, D-Val, Gly, Thr, D-Thr, Asp, D-Asp, γ-carboxylated Asp, Glu, D-Glu, γ-carboxylated Glu, α-aminosuberic acid (Asu), α-aminoadipic acid (Aad), α-aminopimelic acid (Apm), or is absent;

$Xaa_2$ is Asp, γ-carboxylated Asp, Glu, γ-carboxylated Glu, Asu, Aad, Apm, or is absent;

$Xaa_3$ is Asp, γ-carboxylated Asp, Glu, γ-carboxylated Glu, Asu, Aad, Apm, or is absent;

$Xaa_4$ is Cys or D-Cys;

$Xaa_6$ is P-Ser, P-Thr, P-homo-Ser, 4-hydroxyvaline phosphate, P-homo-Thr, P-Cys or P-Tyr;

$Xaa_7$ is Tyr, Leu, Phe or Ile;

$Xaa_8$ is Cys or D-Cys;

$Xaa_{14}$ is Thr, Ala or Phe;

$Xaa_{16}$ is Cys or D-Cys; and $Xaa_{17}$ is Tyr, D-Tyr, or is absent;

wherein:

if $Xaa_1$ is present, $Xaa_1$ may be modified on its amino group by methyl, ethanedioic acid, propanedioic acid, butanedioic acid, pentanedioic acid, hexanedioic acid, heptanedioic acid or octanedioic acid;

if $Xaa_1$ is absent and $Xaa_2$ is present, then $Xaa_2$ may be modified on its amino group by methyl, ethanedioic acid, propanedioic acid, butanedioic acid, pentanedioic acid, hexanedioic acid, heptanedioic acid or octanedioic acid; or if both $Xaa_1$ and $Xaa_2$ are absent, then $Xaa_3$ may be modified on its amino group by methyl, ethanedioic acid, propanedioic acid, butanedioic acid, pentanedioic acid, hexanedioic acid, heptanedioic acid or octanedioic acid.

2. The method according to claim 1, wherein
$Xaa_2$ is Asp, Glu, or absent;
$Xaa_3$ is Asp, Glu, or absent;
$Xaa_7$ is Tyr or Leu;
$Xaa_{14}$ is Thr; and
$Xaa_{17}$ is Tyr or is absent.

3. The method according to claim 1, wherein $Xaa_1$ is Asp, D-Asp, Glu, D-Glu, or absent; and $Xaa_6$ is P-Ser or P-Thr.

4. The method according to claim 3, wherein $Xaa_6$ is P-Ser.

5. The method according to claim 1, wherein $Xaa_1$, $Xaa_2$ and $Xaa_3$ are absent.

6. The method according to claim 1, wherein said peptide comprises the amino acid sequence $Cys_4$ $Cys_5$ P-$Ser_6$ $Xaa_7$ $Cys_8$ $Cys_9$ $Asn_{10}$ $Pro_{11}$ $Ala_{12}$ $Cys_{13}$ $Thr_{14}$ $Gly_{15}$ $Cys_{16}$ $Xaa_{17}$ (SEQ ID NO: 15), wherein $Xaa_7$ is Tyr or Leu, and $Xaa_{17}$ is Tyr, D-Tyr, or is absent.

7. The method according to claim 1, wherein said peptide comprises the amino acid sequence:

```
                                       (SEQ ID NO: 2)
Asp Asp Cys Cys P-Ser Leu Cys Cys Asn Pro Ala Cys
Thr Gly Cys Tyr;

(SEQ ID NO: 3)
Asp Asp Cys Cys P-Ser Leu Cys Cys Asn Pro Ala Cys
Thr Gly Cys;

(SEQ ID NO: 4)
Asp Asp Cys Cys P-Ser Tyr Cys Cys Asn Pro Ala Cys
Thr Gly Cys Tyr;

(SEQ ID NO: 5)
Asp Asp Cys Cys P-Ser Tyr Cys Cys Asn Pro Ala Cys
Thr Gly Cys;

(SEQ ID NO: 6)
Cys Cys P-Ser Leu Cys Cys Asn Pro Ala Cys Thr Gly
Cys Tyr;

(SEQ ID NO: 7)
Cys Cys P-Ser Leu Cys Cys Asn Pro Ala Cys Thr Gly
Cys;

(SEQ ID NO: 8)
Cys Cys P-Ser Tyr Cys Cys Asn Pro Ala Cys Thr Gly
Cys Tyr;
or
                                       (SEQ ID NO: 9)
Cys Cys P-Ser Tyr Cys Cys Asn Pro Ala Cys Thr Gly
Cys.
```

8. The method according to claim 1, wherein the peptide comprises the amino acid sequence Cys Cys P-Ser Leu Cys Cys Asn Pro Ala Cys Thr Gly Cys (SEQ ID NO:7).

9. The method according to claim 1, wherein said peptide or pharmaceutically acceptable salt thereof is isolated.

10. The method according to claim 9, wherein said peptide or pharmaceutically acceptable salt thereof is purified.

11. The method according to claim 1, wherein the pharmaceutical composition further comprises a pharmaceutically acceptable carrier and one or more agents selected from (i) a cation selected from $Mg^{2+}$, $Ca^{2+}$, $Zn^{2+}$, $Mn^{2+}$, $K^+$, $Na^-$ and $Al^{3+}$, and (ii) a sterically hindered primary amine.

12. The method according to claim 11, wherein said agent is $Mg^{2+}$, $Ca^{2+}$, $Zn^{2+}$, $Mn^{2+}$, $K^+$, $Na^-$ or $Al^{3+}$.

13. The method according to claim 11, wherein said agent is a sterically hindered primary amine.

14. The method according to claim 11, wherein the sterically hindered primary amine is an amino acid.

15. The method according to claim 11, wherein the pharmaceutical composition further comprises an antioxidant selected from BHA, vitamin E and propyl gallate.

16. The method according to claim 11, wherein the pharmaceutical composition further comprises a pharmaceutically acceptable binder or additive selected from polyvinyl alcohol, Polyvinylpyrrolidone (povidone), a starch, maltodextrin and a cellulose ether.

17. The method according to claim 11, wherein the pharmaceutical composition further comprises a pharmaceutically acceptable filler selected from cellulose, isomalt, mannitol, lactose and dibasic calcium phosphate.

18. The method according to claim 1, wherein said pharmaceutical composition further comprises an additional therapeutic agent.

19. The method according to claim 18, wherein said additional therapeutic agent is selected from one or more of an analgesic agent, an antidepressant, a promotility or prokinetic agent, an antispasmodic or an additional therapeutic agent to treat constipation.

20. The method according to claim 1, wherein said lower GI disorder is selected from impaired lower intestinal mobility, intestinal or colonic pseudo-obstruction, functional bloating, post-operative ileus, irritable bowel syndrome or constipation.

21. The method according to claim 20, wherein said lower GI disorder is intestinal or colonic pseudo-obstruction.

22. The method according to claim 20, wherein said lower GI disorder is functional bloating.

23. The method according to claim 20, wherein said lower GI disorder is post-operative ileus.

24. The method according to claim 20, wherein said lower GI disorder is irritable bowel syndrome.

25. The method according to claim 24, wherein said irritable bowel syndrome is IBS-C or IBS-M.

26. The method according to claim 1, wherein said constipation is chronic constipation, idiopathic constipation or constipation caused by opiate use.

27. The method according to claim 26, wherein said constipation is chronic constipation.

28. The method according to claim 1, comprising treating or reducing visceral or abdominal pain or discomfort associated with a GI disorder.

29. The method according to claim 28, wherein the GI disorder is irritable bowel syndrome or constipation.

30. The method according to claim 28, wherein the GI disorder is IBS-C or IBS-M.

31. The method according to claim 28, wherein the GI disorder is chronic constipation.

* * * * *